(12) United States Patent
Hassan et al.

(10) Patent No.: US 10,849,640 B2
(45) Date of Patent: Dec. 1, 2020

(54) MEMBRANE AGGREGATING FORCEPS

(71) Applicant: Katalyst Surgical, LLC, Chesterfield, MO (US)

(72) Inventors: Tarek S Hassan, Ann Arbor, MI (US); Eric J Bass, St. Louis, MO (US); Gregg D Scheller, Wildwood, MO (US)

(73) Assignee: KATALYST SURGICAL, LLC, Chesterfield, MO (US)

( * ) Notice: Subject to any disclaimer, the term of this patent is extended or adjusted under 35 U.S.C. 154(b) by 124 days.

(21) Appl. No.: 15/987,780

(22) Filed: May 23, 2018

(65) Prior Publication Data
US 2019/0357928 A1 Nov. 28, 2019

(51) Int. Cl.
| A61B 17/28 | (2006.01) |
| A61F 9/007 | (2006.01) |
| A61B 17/00 | (2006.01) |
| A61B 90/00 | (2016.01) |

(52) U.S. Cl.
CPC ........ A61B 17/282 (2013.01); A61B 17/2841 (2013.01); A61F 9/007 (2013.01); *A61B 2017/0046* (2013.01); *A61B 2090/061* (2016.02)

(58) Field of Classification Search
CPC ....... A61B 17/28; A61B 17/30; A61B 17/282; A61B 17/2812; A61B 17/2841; A61F 9/007; A61F 9/00736
See application file for complete search history.

(56) References Cited

U.S. PATENT DOCUMENTS

| 1,371,288 A | 3/1921 | Wolhaupter |
| 1,736,731 A | 11/1929 | Breeding |
| 2,549,731 A | 4/1951 | Wattley |
| (Continued) | | |

FOREIGN PATENT DOCUMENTS

| WO | WO1997015234 A1 | 5/1997 |
| WO | WO1998037819 A1 | 9/1998 |
| (Continued) | | |

OTHER PUBLICATIONS

Steve Charles, Techniques and tools for dissection of epiretinal membranes, Graefe Arch Clin Exp Ophthalmol, 241:347-352, 2003.
(Continued)

*Primary Examiner* — Tuan V Nguyen

(57) ABSTRACT

A membrane aggregating forceps may include a blank, a membrane aggregating forceps tip of the blank, a hypodermic tube, and an actuation structure. The blank may be disposed in the hypodermic tube and the actuation structure wherein a compression of the actuation structure is configured to close the membrane aggregating forceps tip and wherein a decompression of the actuation structure is configured to open the membrane aggregating forceps tip. The membrane aggregating forceps tip may include a first membrane aggregating forceps jaw having a first curved medial projection and a second membrane aggregating forceps jaw having a second curved medial projection. The first curved medial projection may include a first membrane socket, a first membrane aggregating fillet, and a first blunt edge. The second curved medial projection may include a second membrane socket, a second membrane aggregating filled, and a second blunt edge.

19 Claims, 11 Drawing Sheets

(56) References Cited

U.S. PATENT DOCUMENTS

| | | |
|---|---|---|
| 3,659,607 A | 5/1972 | Banko |
| 4,135,868 A | 1/1979 | Schainholz |
| 4,504,264 A | 3/1985 | Kelman |
| 4,541,992 A | 9/1985 | Jerge et al. |
| 4,553,957 A | 11/1985 | Williams et al. |
| 4,610,252 A | 9/1986 | Catalano |
| 4,706,666 A | 11/1987 | Sheets |
| 4,739,761 A | 4/1988 | Grandon |
| 4,798,292 A | 1/1989 | Hauze |
| 4,959,199 A | 9/1990 | Brewer |
| 5,190,050 A | 3/1993 | Nitzsche |
| 5,215,726 A | 6/1993 | Kudla et al. |
| 5,222,973 A | 6/1993 | Shame et al. |
| 5,227,313 A | 7/1993 | Gluck et al. |
| 5,286,255 A | 2/1994 | Webber |
| 5,318,589 A | 6/1994 | Lichtman |
| 5,346,677 A | 9/1994 | Risk |
| 5,355,871 A | 10/1994 | Hurley et al. |
| 5,370,658 A | 12/1994 | Scheller et al. |
| 5,384,103 A | 1/1995 | Miller |
| 5,415,645 A | 5/1995 | Friend et al. |
| 5,425,730 A | 6/1995 | Luloh |
| 5,433,929 A | 7/1995 | Riihimaki et al. |
| 5,451,230 A | 9/1995 | Steinert |
| 5,527,313 A | 6/1996 | Scott et al. |
| 5,601,581 A | 2/1997 | Fogarty et al. |
| 5,636,639 A | 6/1997 | Turturro et al. |
| 5,647,115 A | 7/1997 | Slater et al. |
| 5,695,514 A | 12/1997 | Chin |
| D393,067 S | 3/1998 | Geary et al. |
| D393,715 S | 4/1998 | Strickland |
| 5,759,502 A | 6/1998 | Spencer et al. |
| 5,792,165 A | 8/1998 | Klieman et al. |
| 5,810,811 A | 9/1998 | Yates et al. |
| 5,843,387 A | 12/1998 | Dane et al. |
| 5,851,197 A | 12/1998 | Marano et al. |
| 5,893,873 A | 4/1999 | Rader et al. |
| 5,893,877 A | 4/1999 | Gampp, Jr. et al. |
| 5,913,422 A | 6/1999 | Cote et al. |
| 5,916,159 A | 6/1999 | Ryan, Jr. |
| 5,921,998 A | 7/1999 | Tano et al. |
| 6,099,550 A | 8/2000 | Yoon |
| 6,159,162 A | 12/2000 | Kostylev et al. |
| 6,183,467 B1 | 2/2001 | Shapeton et al. |
| 6,277,100 B1 | 8/2001 | Raulerson et al. |
| D453,222 S | 1/2002 | Garito et al. |
| 6,419,675 B1 | 7/2002 | Gallo, Sr. |
| D463,555 S | 9/2002 | Etter et al. |
| 6,451,037 B1 | 9/2002 | Chandrasekaran et al. |
| 6,488,695 B1 | 12/2002 | Hickingbotham |
| 6,551,129 B2 | 4/2003 | Kato |
| 6,572,565 B2 | 6/2003 | Daley et al. |
| 6,575,989 B1 | 6/2003 | Scheller et al. |
| 6,592,603 B2 | 7/2003 | Lasner |
| 6,616,683 B1 | 9/2003 | Toth et al. |
| 6,730,076 B2 | 5/2004 | Hickingbotham |
| 6,749,601 B2 | 6/2004 | Chin |
| 6,772,765 B2 | 8/2004 | Scheller et al. |
| 6,800,076 B2 | 10/2004 | Humayun |
| 6,863,668 B2 | 3/2005 | Gillespie et al. |
| 6,908,476 B2 | 6/2005 | Jud et al. |
| 6,926,728 B2 | 8/2005 | Zucherman et al. |
| 6,945,984 B2 | 9/2005 | Arumi et al. |
| 7,338,494 B2 | 3/2008 | Ryan |
| 7,344,553 B2 | 3/2008 | Opolski et al. |
| D565,733 S | 4/2008 | Andre |
| 7,438,717 B2 | 10/2008 | Tylke |
| 7,632,242 B2 | 12/2009 | Griffin et al. |
| 7,731,728 B2 | 6/2010 | Glaser |
| 7,783,346 B2 | 8/2010 | Smith et al. |
| D625,412 S | 10/2010 | Garito et al. |
| 7,766,904 B2 | 10/2010 | Mc Gowan, Sr. et al. |
| 7,935,080 B2 | 5/2011 | Howell et al. |
| 8,038,692 B2 | 10/2011 | Valencia et al. |
| 8,197,468 B2 | 6/2012 | Scheller et al. |
| 8,202,288 B2 | 6/2012 | Ryan |
| 8,262,682 B2 | 9/2012 | Terao |
| 8,821,444 B2 | 9/2014 | Scheller et al. |
| 9,138,346 B2 | 9/2015 | Scheller et al. |
| 9,149,389 B2 | 10/2015 | Scheller et al. |
| 9,204,995 B2 | 12/2015 | Scheller et al. |
| 9,226,762 B2 | 1/2016 | Scheller et al. |
| 9,427,251 B2 | 8/2016 | Rethy et al. |
| 2001/0056286 A1 | 12/2001 | Etter et al. |
| 2002/0115902 A1 | 8/2002 | Dejuan, Jr. et al. |
| 2003/0171762 A1 | 9/2003 | Forchette et al. |
| 2003/0229976 A1 | 12/2003 | Scheller et al. |
| 2005/0021010 A1 | 1/2005 | Rothweiler et al. |
| 2005/0154403 A1 | 7/2005 | Sauer et al. |
| 2005/0245950 A1 | 11/2005 | Kozlowski |
| 2006/0036270 A1 | 2/2006 | Terao |
| 2006/0235382 A1 | 10/2006 | Cohen et al. |
| 2007/0104609 A1 | 5/2007 | Powell |
| 2007/0106246 A1 | 5/2007 | Modesitt |
| 2007/0167939 A1 | 7/2007 | Duong et al. |
| 2007/0185514 A1 | 8/2007 | Kirchhevel |
| 2007/0282348 A1 | 12/2007 | Lumpkin |
| 2008/0183199 A1 | 7/2008 | Attinger |
| 2008/0195135 A1 | 8/2008 | Attinger |
| 2008/0255526 A1 | 10/2008 | Bosse et al. |
| 2009/0030427 A1 | 1/2009 | Razvi et al. |
| 2009/0112258 A1 | 4/2009 | Kreidler |
| 2009/0131870 A1 | 5/2009 | Fiser |
| 2009/0228066 A1 | 10/2009 | Hirata et al. |
| 2009/0318856 A1 | 12/2009 | Glaser |
| 2010/0023050 A1 | 1/2010 | Reinauer et al. |
| 2010/0063359 A1 | 3/2010 | Okoniewski |
| 2010/0145381 A1 | 6/2010 | Moon |
| 2010/0228226 A1 | 9/2010 | Nielsen |
| 2011/0015669 A1 | 1/2011 | Corcosteugi |
| 2011/0071346 A1 | 3/2011 | Morningstar |
| 2012/0016413 A1 | 1/2012 | Timm et al. |
| 2012/0116361 A1 | 5/2012 | Hanlon et al. |
| 2012/0150216 A1 | 6/2012 | Hickingbotham et al. |
| 2012/0179172 A1 | 7/2012 | Paul, Jr. et al. |
| 2012/0191120 A1 | 7/2012 | Linsi |
| 2013/0071507 A1 | 3/2013 | Scheller et al. |
| 2013/0085326 A1 | 4/2013 | Scheller et al. |
| 2013/0197488 A1 | 8/2013 | Scheller et al. |
| 2014/0005700 A1 | 1/2014 | Casey et al. |
| 2014/0012314 A1 | 1/2014 | Dai et al. |
| 2014/0066977 A1 | 3/2014 | Scheller et al. |
| 2014/0121697 A1 | 5/2014 | Scheller et al. |
| 2014/0128909 A1 | 5/2014 | Scheller et al. |
| 2014/0135820 A1 | 5/2014 | Schaller et al. |
| 2014/0142603 A1 | 5/2014 | Scheller et al. |
| 2014/0163363 A1 | 6/2014 | Scheller et al. |
| 2014/0172010 A1 | 6/2014 | Vezzu |
| 2014/0276981 A1 | 9/2014 | Hendricksen et al. |
| 2014/0277110 A1 | 9/2014 | Scheller et al. |
| 2015/0088193 A1 | 3/2015 | Scheller et al. |
| 2015/0173944 A1 | 6/2015 | Linsi et al. |
| 2015/0297278 A1 | 10/2015 | Scheller |
| 2016/0296246 A1* | 10/2016 | Schaller ............... A61B 17/30 |
| 2017/0079675 A1 | 3/2017 | Scheller et al. |
| 2017/0086871 A1* | 3/2017 | Scheller ............... A61B 17/30 |
| 2017/0100114 A1 | 4/2017 | Scheller et al. |
| 2017/0340380 A1 | 11/2017 | Scheller et al. |
| 2017/0361034 A1 | 12/2017 | Scheller et al. |
| 2018/0014849 A1 | 1/2018 | Scheller et al. |

FOREIGN PATENT DOCUMENTS

| | | |
|---|---|---|
| WO | WO2002041796 A2 | 5/2002 |
| WO | WO2014140808 A1 | 9/2014 |
| WO | WO2015026957 A1 | 2/2015 |
| WO | WO2017066026 A1 | 4/2017 |
| WO | WO2017218161 A1 | 12/2017 |
| WO | WO2018017296 A1 | 1/2018 |

(56) References Cited

OTHER PUBLICATIONS http://www.bpf.co.uk/plastipedia/polymers/polyamides.aspx [Mar. 20, 2017 4:57:01 PM].
Cummins, Kate, The rise of additive manufacturing, (May 24, 2010); https://www.theengineer.co.uk/issues/24-may-2010/the-rise-of-additive-manufacturing/.

\* cited by examiner

MEMBRANE AGGREGATING FORCEPS

FIELD OF THE INVENTION

The present disclosure relates to a surgical instrument, and, more particularly, to a microsurgical forceps.

BACKGROUND OF THE INVENTION

A microsurgical forceps may be used to perform a microsurgical procedure, e.g., an ophthalmic surgical procedure. For example, a surgeon may use a forceps to grasp and manipulate tissues or other surgical instruments to perform portions of a surgical procedure. A particular microsurgical procedure may require a surgeon to separate a first tissue from a second tissue without causing trauma to at least one of the tissues. Such a separation procedure may be particularly difficult for a surgeon to perform if the tissue surface geometry is not flat, e.g., if the tissue surface geometry is convex. For example, an ophthalmic surgeon may be required to remove an internal limiting membrane from a patient's retina without causing trauma to the patient's retina. Accordingly, there is a need for a microsurgical forceps that enables a surgeon to separate a first tissue from a second tissue without causing significant trauma to at least one of the tissues.

BRIEF SUMMARY OF THE INVENTION

The present disclosure provides a membrane aggregating forceps. In one or more embodiments, a membrane aggregating forceps may comprise a blank, a membrane aggregating forceps tip of the blank, a hypodermic tube, and an actuation structure. Illustratively, the blank may be disposed in the hypodermic tube and the actuation structure wherein a compression of the actuation structure is configured to close the membrane aggregating forceps tip and wherein a decompression of the actuation structure is configured to open the membrane aggregating forceps tip. In one or more embodiments, the membrane aggregating forceps tip may comprise a first membrane aggregating forceps jaw having a first curved medial projection and a second membrane aggregating forceps jaw having a second curved medial projection. Illustratively, the first curved medial projection may comprise a first membrane socket, a first membrane aggregating fillet, and a first blunt edge. In one or more embodiments, the second curved medial projection may comprise a second membrane socket, a second membrane aggregating filled, and a second blunt edge.

BRIEF DESCRIPTION OF THE DRAWINGS

The above and further advantages of the present invention may be better understood by referring to the following description in conjunction with the accompanying drawings in which like reference numerals indicate identical or functionally similar elements.

DETAILED DESCRIPTION OF AN ILLUSTRATIVE EMBODIMENT

Figure 1A:
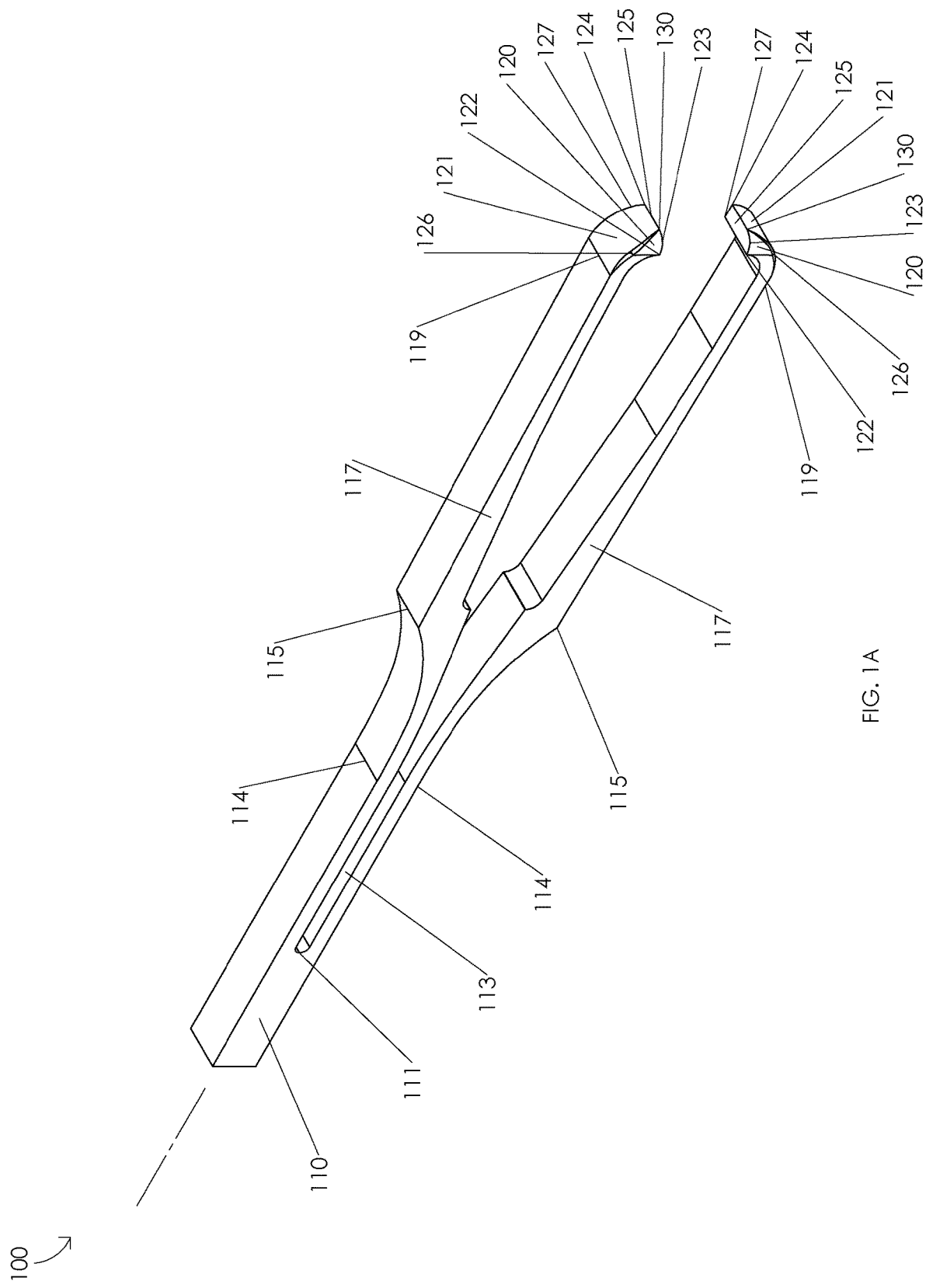
FIGS. 1A, 1B, 1C, 1D, 1E, 1F, and 1G are schematic diagrams illustrating a membrane aggregating forceps tip.
Figure 1B:
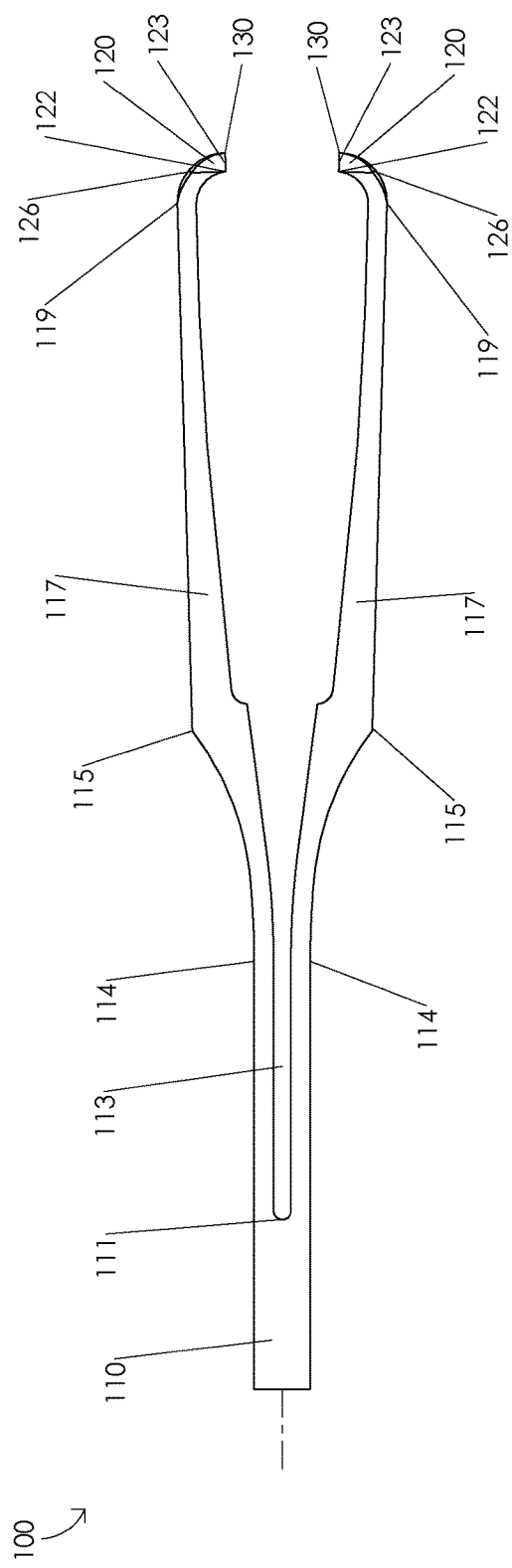
Figure 1C:
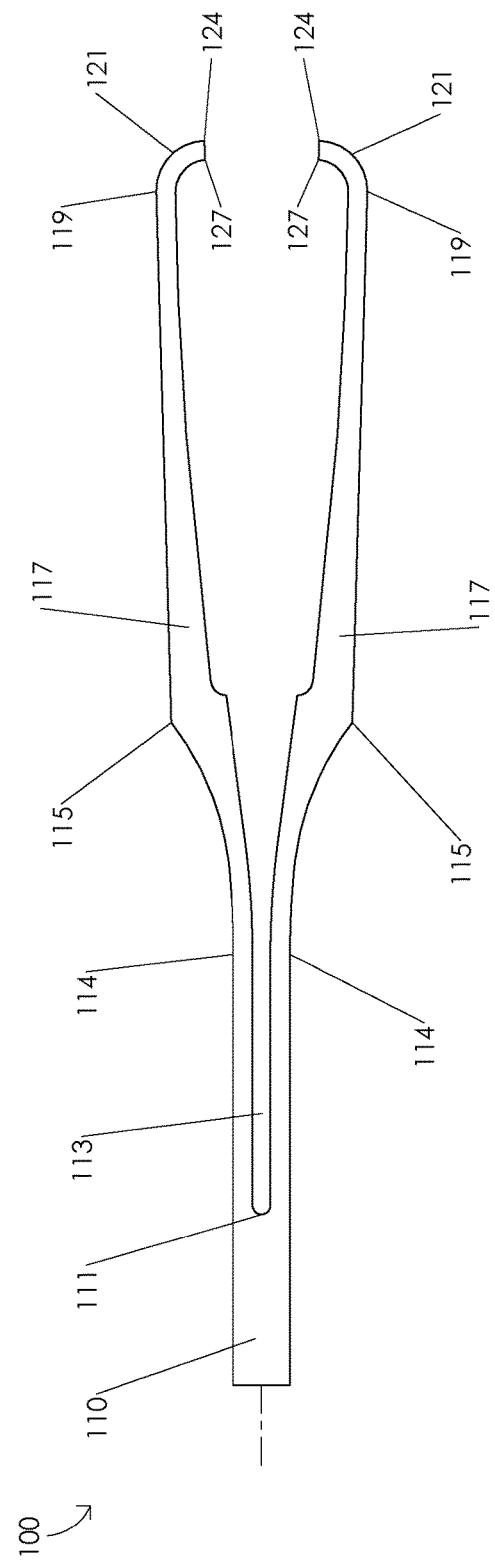
Figure 1E:
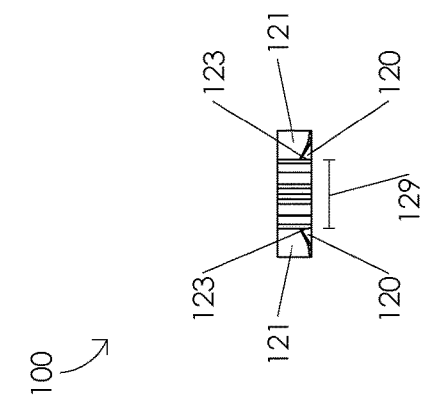
Figure 1D:
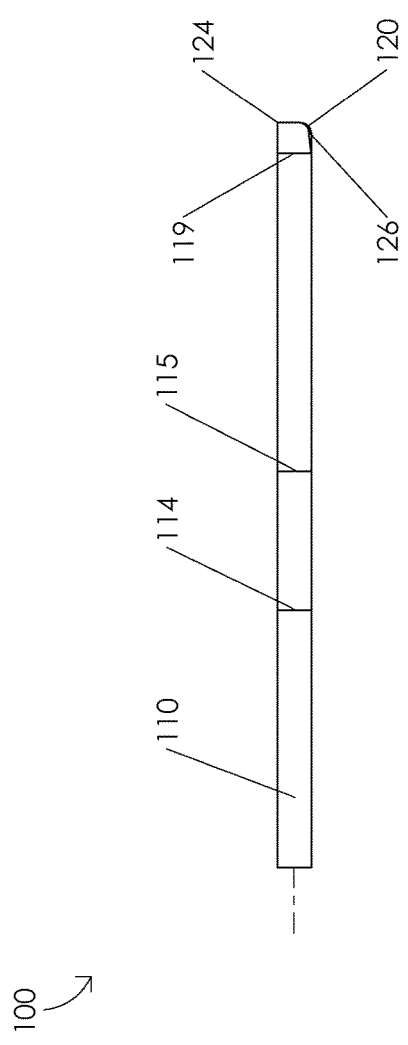
Figure 1G:
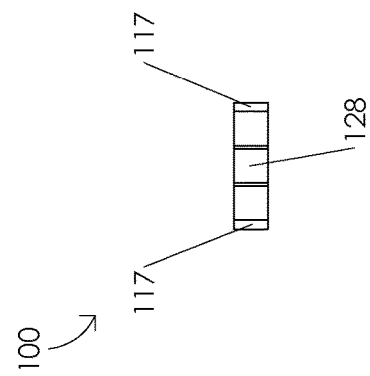
Figure 1F:
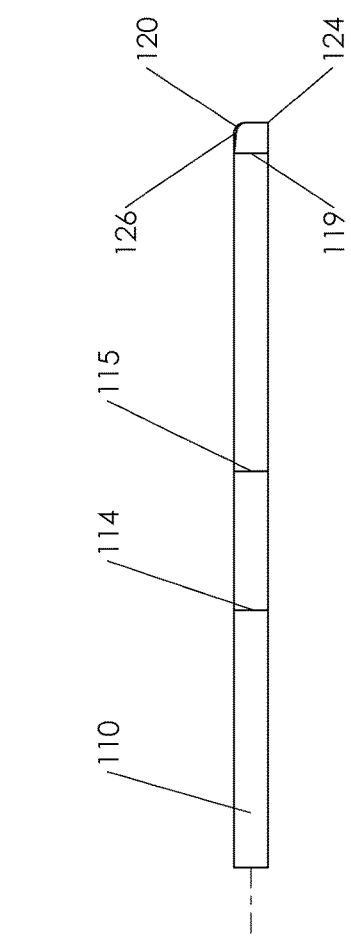

FIGS. 1A, 1B, 1C, 1D, 1E, 1F, and 1G are schematic diagrams illustrating a membrane aggregating forceps tip 100. FIG. 1A illustrates an isometric view of a membrane aggregating forceps tip 100. FIG. 1B illustrates a bottom view of a membrane aggregating forceps tip 100. FIG. 1C illustrates a top view of a membrane aggregating forceps tip 100. FIG. 1D illustrates a side view of a membrane aggregating forceps tip 100. FIG. 1E illustrates a front view of a membrane aggregating forceps tip 100. FIG. 1F illustrates a side view of a membrane aggregating forceps tip 100 rotated 180 degrees. FIG. 1G illustrates a back view of a membrane aggregating forceps tip 100. In one or more embodiments, a membrane aggregating forceps tip 100 may comprise a first membrane aggregating forceps jaw 117 and a second membrane aggregating forceps jaw 117.

Illustratively, membrane aggregating forceps tip 100 may comprise a blank 110 and a blank aperture 113. In one or more embodiments, blank aperture 113 may comprise a blank aperture proximal end 111. Illustratively, membrane aggregating forceps tip 100 may comprise a first jaw spring 114 and a second jaw spring 114. In one or more embodiments, membrane aggregating forceps tip 100 may comprise a first jaw shoulder 115 and a second jaw shoulder 115. Illustratively, membrane aggregating forceps tip 100 may comprise a first curved medial projection 121 having a first curved medial projection proximal end 119 and a second curved medial projection 121 having a second curved medial projection proximal end 119. In one or more embodiments, membrane aggregating forceps tip 100 may comprise a first membrane socket 120 and a second membrane socket 120. Illustratively, membrane aggregating forceps tip 100 may comprise a first proximal membrane aggregating vertex 122 and a second proximal membrane aggregating vertex 122. In one or more embodiments, membrane aggregating forceps tip 100 may comprise a first membrane aggregating fillet 123 and a second membrane aggregating fillet 123. Illustratively, membrane aggregating forceps tip 100 may comprise a first distal jaw vertex 124 and a second distal jaw vertex 124. In one or more embodiments, membrane aggregating forceps tip 100 may comprise a first medial jaw surface 125 and a second medial jaw surface 125. Illustratively, membrane aggregating forceps tip 100 may comprise a first blunt edge 126 and a second blunt edge 126. In one or more embodiments, membrane aggregating forceps tip 100 a first proximal jaw vertex 127 and a second proximal jaw vertex 127. Illustratively, membrane aggregating forceps tip 100 may comprise a first distal membrane aggregating vertex 130 and a second distal membrane aggregating vertex 130. In one or more embodiments, membrane aggregating forceps tip 100 may comprise a blank proximal end 128.

Illustratively, membrane aggregating forceps tip 100 may comprise a membrane aggregating forceps jaw maximum separation distance 129. In one or more embodiments, membrane aggregating forceps jaw maximum separation distance 129 may be a distance in a range of 0.017 to 0.023 inches, e.g., membrane aggregating forceps jaw maximum separation distance 129 may be a distance of 0.020 inches. Illustratively, membrane aggregating forceps jaw maximum separation distance 129 may be a distance of less than 0.017 inches or greater than 0.023 inches. In one or more embodiments, membrane socket 120 may comprise a radial diameter in a range of 0.002 to 0.004 inches, e.g., membrane socket 120 may comprise a radial diameter of 0.003 inches. Illustratively, membrane socket 120 may comprise a radial diameter of less than 0.002 inches or greater than 0.004 inches. In one or more embodiments, membrane aggregating fillet 123 may comprise a radial diameter in a range of 0.004 to 0.006 inches, e.g., membrane aggregating fillet 123 may comprise a radial diameter of 0.005 inches. Illustratively, membrane aggregating fillet 123 may comprise a radial diameter of less than 0.004 inches or greater than 0.006 inches. In one or more embodiments, blank aperture 113 may have a width in a range of 0.0020 to 0.0030 inches, e.g., blank aperture 113 may have a width of 0.0025 inches. Illustratively, blank aperture 113 may have a width of less than 0.0020 inches or greater than 0.0030 inches. In one or more embodiments, curved medial projection 121 may have an axial length in a range of 0.005 to 0.009 inches, e.g., curved medial projection 121 may have an axial length of 0.007 inches. Illustratively, curved medial projection 121 may have an axial length of less than 0.005 inches or greater than 0.009 inches.

In one or more embodiments, blank aperture 113 may be disposed between first jaw spring 114 and second jaw spring 114, e.g., blank aperture 113 may be disposed between first membrane aggregating forceps jaw 117 and second membrane aggregating forceps jaw 117. Illustratively, jaw spring 114 may be disposed between blank aperture proximal end 111 and jaw shoulder 115. In one or more embodiments, jaw shoulder 115 may be disposed between jaw spring 114 and curved medial projection 121, e.g., jaw shoulder 115 may be disposed between jaw spring 114 and curved medial projection proximal end 119. Illustratively, membrane aggregating fillet 123 may be disposed between proximal membrane aggregating vertex 122 and distal membrane aggregating vertex 130, e.g., membrane aggregating fillet 123 may be disposed between membrane socket 120 and medial jaw surface 125. In one or more embodiments, membrane socket 120 may be disposed between membrane aggregating fillet 123 and blunt edge 126, e.g., membrane socket 120 may be disposed between blunt edge 126 and proximal membrane aggregating vertex 122. Illustratively, blunt edge 126 may be disposed between curved medial projection proximal end 119 and distal membrane aggregating vertex 130, e.g., blunt edge 126 may be disposed between curved medial projection proximal end 119 and medial jaw surface 125.

In one or more embodiments, membrane socket 120 may be disposed between curved medial projection proximal end 119 and distal membrane aggregating vertex 130, e.g., membrane socket 120 may be disposed between curved medial projection proximal end 119 and medial jaw surface 125. Illustratively, medial jaw surface 125 may be disposed between proximal membrane aggregating vertex 122 and proximal jaw vertex 127, e.g., medial jaw surface 125 may be disposed between proximal membrane aggregating vertex 122 and distal jaw vertex 124. In one or more embodiments, medial jaw surface 125 may be disposed between proximal membrane aggregating vertex 122 and distal membrane aggregating vertex 130, e.g., medial jaw surface 125 may be disposed between proximal membrane aggregating vertex 122 and membrane aggregating fillet 123. Illustratively, medial jaw surface 125 may be disposed between proximal jaw vertex 127 and distal jaw vertex 124, e.g., medial jaw surface 125 may be disposed between proximal jaw vertex 127 and distal membrane aggregating vertex 130. In one or more embodiments, medial jaw surface 125 may be disposed between proximal jaw vertex 127 and membrane aggregating fillet 123, e.g., medial jaw surface 125 may be disposed between proximal jaw vertex 127 and membrane socket 120. Illustratively, medial jaw surface 125 may be disposed between distal jaw vertex 124 and distal membrane aggregating vertex 130, e.g., medial jaw surface 125 may be disposed between distal jaw vertex 124 and membrane aggregating fillet 123.

Illustratively, membrane aggregating forceps tip 100 may be manufactured with dimensions configured for performing microsurgical procedures, e.g., ophthalmic surgical procedures. In one or more embodiments, membrane aggregating forceps tip 100 may be manufactured from a blank 110. In one or more embodiments, tapered membrane removing forceps tip 100 may be manufactured by modifying blank 110, e.g., with an electric discharge machine, a laser, a file, deep reactive ion etching, or any suitable modification means. Illustratively, membrane aggregating forceps tip 100 may be manufactured by an additive manufacturing process, e.g., membrane aggregating forceps tip 100 may be manufactured by a 3D printing process. For example, membrane aggregating forceps tip 100 may be manufactured by selective laser sintering, selective heat sintering, selective laser melting, electron-beam melting, direct metal laser sintering, electron beam freeform fabrication, etc.

Figure 2A:
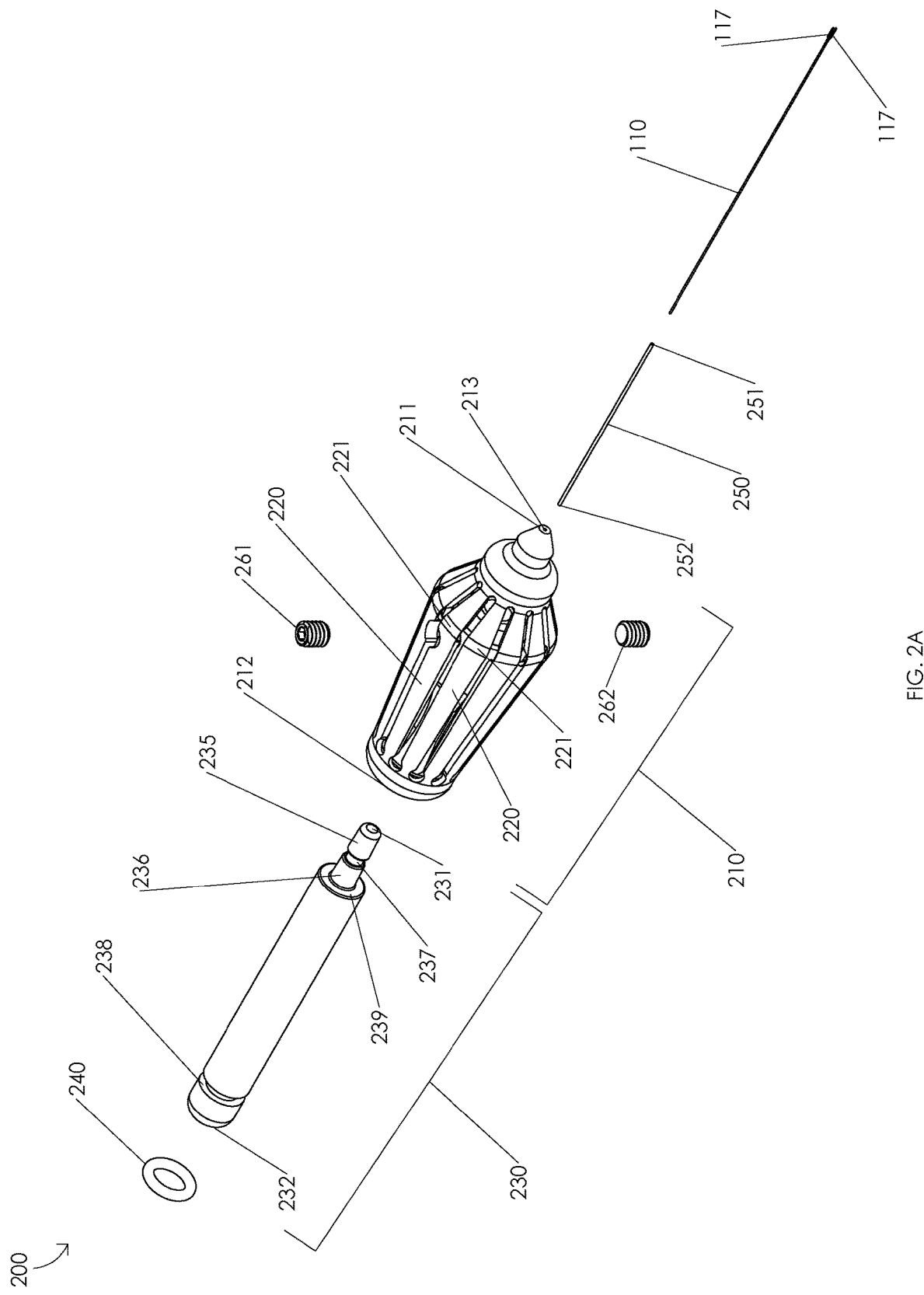
FIG. 2A is a schematic diagram illustrating an exploded view of a membrane aggregating forceps assembly.

FIG. 2A is a schematic diagram illustrating an exploded view of a membrane aggregating forceps assembly 200. Illustratively, a membrane aggregating forceps assembly 200 may comprise an actuation structure 210, a removable handle 230, a gage indicator 240, a hypodermic tube 250, a blank 110, a superior setscrew 261, and an inferior setscrew 262. In one or more embodiments, an actuation structure 210 may comprise an actuation structure distal end 211, an actuation structure proximal end 212, a plurality of actuation arms 220, and a hypodermic tube housing 213. Illustratively, each actuation arm 220 of actuation structure 210 may comprise at least one extension mechanism 221. In one or more embodiments, removable handle 230 may comprise a removable handle distal end 231, a removable handle proximal end 232, a barb head 235, a barb base 236, a barb channel 237, a gage indicator housing 238, and an actuation structure interface 239. Illustratively, hypodermic tube 250 may comprise a hypodermic tube distal end 251 and a hypodermic tube proximal end 252. In one or more embodiments, blank 110 may comprise a membrane aggregating forceps tip 100.

Figure 2B:
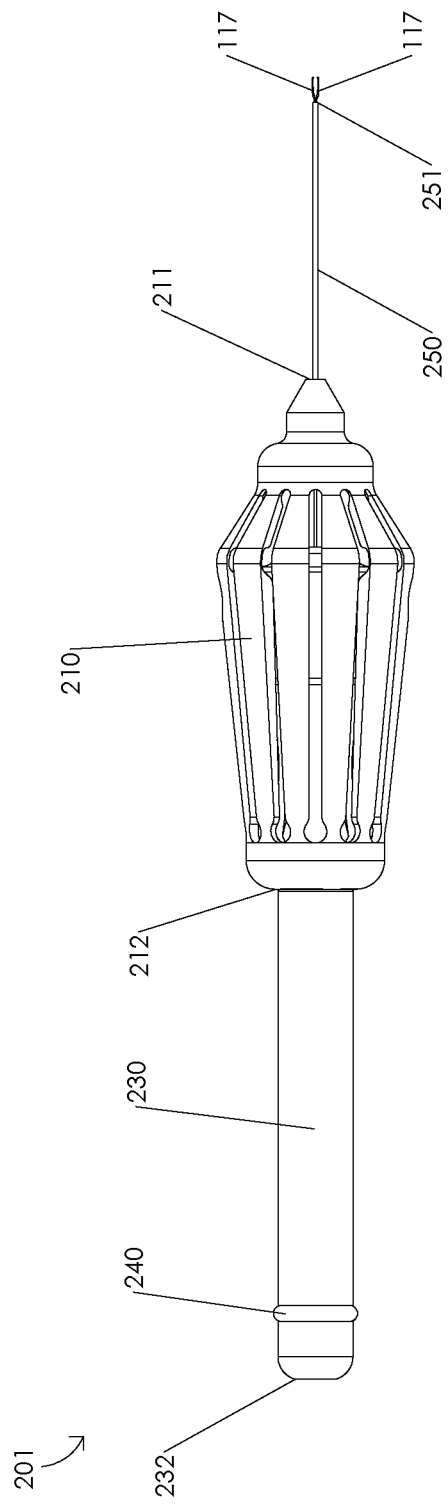
FIGS. 2B and 2C are schematic diagrams illustrating an assembled membrane aggregating forceps.
Figure 2C:
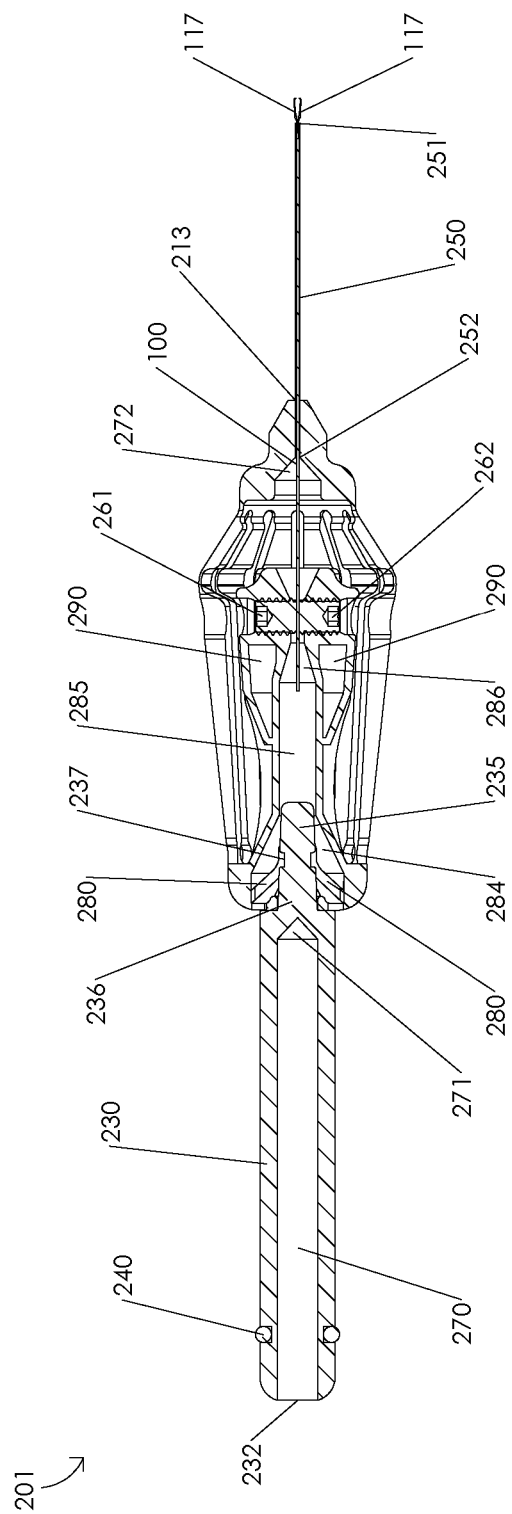

FIGS. 2B and 2C are schematic diagrams illustrating an assembled membrane aggregating forceps 201. FIG. 2B illustrates a side view of an assembled membrane aggregating forceps 201. FIG. 2C illustrates a cross-sectional view in a sagittal plane of an assembled membrane aggregating forceps 201. Illustratively, gage indicator 240 may be disposed within gage indicator housing 238. In one or more embodiments, gage indicator 240 may be configured to visually indicate a size of hypodermic tube 250, e.g., gage indicator 240 may comprise a ring colored to visually indicate an outer diameter of hypodermic tube 250. Illustratively, removable handle 230 may comprise an inner bore 270 and an inner bore distal taper 271. In one or more embodiments, inner bore 270 may have an inner bore distal end and an inner bore proximal end wherein the inner bore proximal end is adjacent to the removable handle proximal end 232.

Illustratively, inner bore distal taper 271 may be disposed between a distal end of inner bore 270 and barb base 236. In one or more embodiments, actuation structure 210 may comprise an inner nosecone 272, a plurality of fingers 280, an inner chamber proximal taper 284, an inner chamber 285, an inner chamber distal taper 286, and a setscrew housing 290. Illustratively, inner nosecone 272 may be disposed between setscrew housing 290 and actuation structure distal end 211. In one or more embodiments, setscrew housing 290 may be disposed between inner chamber distal taper 286 and inner nosecone 272. Illustratively, inner chamber distal taper 286 may be disposed between inner chamber 285 and setscrew housing 290. In one or more embodiments, inner chamber 285 may be disposed between inner chamber proximal taper 284 and inner chamber distal taper 286. Illustratively, each finger 280 of the plurality of fingers 280 may be disposed in inner chamber proximal taper 284.

Illustratively, a portion of removable handle 230 may be disposed within a portion of actuation structure 210, e.g., removable handle distal end 231 may be disposed within actuation structure 210. In one or more embodiments, barb head 235 may be disposed within actuation structure 210 wherein barb head 235 is disposed in inner chamber 285 and inner chamber proximal taper 284. Illustratively, barb base 236 may be disposed within actuation structure 210 wherein barb base 236 is disposed in inner chamber proximal taper 284. In one or more embodiments, barb channel 237 may be disposed within actuation structure 210 wherein barb channel 237 is disposed in inner chamber proximal taper 284. Illustratively, each finger 280 of the plurality of fingers 280 may be partially disposed in barb channel 237.

In one or more embodiments, a portion of removable handle 230 may be temporarily fixed within actuation structure 210, e.g., barb head 235, barb base 236, and barb channel 237 may be temporarily fixed within actuation structure 210. Illustratively, each finger 280 of the plurality of fingers 280 may be configured to temporarily fix a portion of removable handle 230 within actuation structure 210. In one or more embodiments, each finger 280 of the plurality of fingers 280 may be configured to temporarily fix a portion of removable handle 230 within actuation structure 210 by a snap fit, e.g., each finger 280 of the plurality of fingers 280 may be configured to temporarily fix a portion of removable handle 230 within actuation structure 210 by a torsional snap fit. Illustratively, a portion of removable handle 230 may be temporarily fixed within actuation structure 210 by a force of friction, e.g., a portion of removable handle 230 may be temporarily fixed within actuation structure 210 by an interference fit. In one or more embodiments, a portion of removable handle 230 may be disposed within a portion of actuation structure 210 wherein actuation structure interface 239 is adjacent to actuation structure proximal end 212.

Illustratively, a surgeon may optionally remove a portion of removable handle 230 from a portion of actuation structure 210. For example, a surgeon may optionally remove removable handle 230 from actuation structure 210 to grasp actuation structure wherein a portion of the surgeon's palm is adjacent to actuation structure proximal end 212. In one or more embodiments, a surgeon may optionally remove removable handle 230 from actuation structure 210 by pulling removable handle 230 out from inner chamber proximal taper 284. Illustratively, a surgeon may optionally insert removable handle 230 into actuation structure 210 by pushing removable handle 230 into inner chamber proximal taper 284. In one or more embodiments, a surgeon may perform a first portion of a surgical procedure with removable handle 230 disposed within actuation structure 210. Illustratively, the surgeon may perform a second portion of the surgical procedure with removable handle 230 removed from actuation structure 210. In one or more embodiments, the surgeon may perform a third portion of the surgical procedure with removable handle 230 disposed within actuation structure 210. Illustratively, the surgeon may perform a fourth portion of the surgical procedure with removable handle 230 removed from actuation structure 210.

In one or more embodiments, a portion of hypodermic tube 250 may be disposed in a portion of actuation structure 210, e.g., hypodermic tube proximal end 252 may be disposed in a portion of actuation structure 210. Illustratively, a portion of hypodermic tube 250 may be disposed in hypodermic tube housing 213, e.g., hypodermic tube proximal end 252 may be disposed in hypodermic tube housing 213. In one or more embodiments, a portion of hypodermic tube 250 may be fixed within a portion of actuation structure 210, e.g., a portion of hypodermic tube 250 may be fixed within a portion of actuation structure 210 by an adhesive, a weld, a force of friction, etc.

Illustratively, blank 110 may be disposed in hypodermic tube 250 and actuation structure 210, e.g., blank 110 may be disposed in hypodermic tube 250 an actuation structure 210 wherein blank proximal end 128 is disposed in actuation structure 210. In one or more embodiments, blank 110 may be disposed in hypodermic tube 250, inner nosecone 272, setscrew housing 290, inner chamber distal taper 286, and inner chamber 285. Illustratively, superior setscrew 261 and inferior setscrew 262 may be disposed within setscrew housing 290. In one or more embodiments, blank 110 may be fixed in a position relative to actuation structure proximal end 212 and hypodermic tube 250, e.g., superior setscrew 261 and inferior setscrew 262 may be configured to fix blank 110 in a position relative to actuation structure proximal end 212 and hypodermic tube 250. Illustratively, a portion of blank 110 may be disposed between superior setscrew 261 and inferior setscrew 262 wherein the portion of blank 110 is fixed in a position relative to actuation structure proximal end 212 and hypodermic tube 250 by a force applied to the portion of blank 110 by superior setscrew 261 and inferior setscrew 262.

In one or more embodiments, a compression of actuation structure 210 may be configured to extend actuation structure distal end 211 relative to actuation structure proximal end 212. Illustratively, a compression of actuation structure 210 may be configured to extend hypodermic tube 250 relative to blank 110. In one or more embodiments, a compression of actuation structure 210 may be configured to extend hypodermic tube distal end 251 over a portion of first and second membrane aggregating forceps jaws 117, e.g., a compression of actuation structure 210 may be configured to extend hypodermic tube distal end 251 over a portion of first membrane aggregating forceps jaw 117 disposed between first jaw spring 114 and first jaw shoulder 115. For example, a compression of actuation structure 210 may be configured to extend hypodermic tube distal end 251 over a portion of second membrane aggregating forceps jaw 117 disposed between second jaw spring 114 and second jaw shoulder 115. Illustratively, a compression of actuation structure 210 may be configured to decrease a distance between first medial jaw surface 125 and second medial jaw surface 125. In one or more embodiments, a compression of actuation structure 210 may be configured to close membrane aggregating forceps tip 100.

In one or more embodiments, a decompression of actuation structure 210 may be configured to retract actuation structure distal end 211 relative to actuation structure proximal end 212. Illustratively, a decompression of actuation structure 210 may be configured to retract hypodermic tube 250 relative to blank 110. In one or more embodiments, a decompression of actuation structure 210 may be configured to retract hypodermic tube distal end 251 off of a portion of first and second membrane aggregating forceps jaws 117, e.g., a decompression of actuation structure 210 may be configured to retract hypodermic tube distal end 251 off of a portion of first membrane aggregating forceps jaw 117 disposed between first jaw spring 114 and first jaw shoulder 115. For example, a decompression of actuation structure 210 may be configured to retract hypodermic tube distal end 251 off of a portion of second membrane aggregating forceps jaw 117 disposed between second jaw spring 114 and second jaw shoulder 115. Illustratively, a decompression of actuation structure 210 may be configured to increase a distance between first medial jaw surface 125 and second medial jaw surface 125. In one or more embodiments, a decompression of actuation structure 210 may be configured to open membrane aggregating forceps tip 100.

Figure 3A:
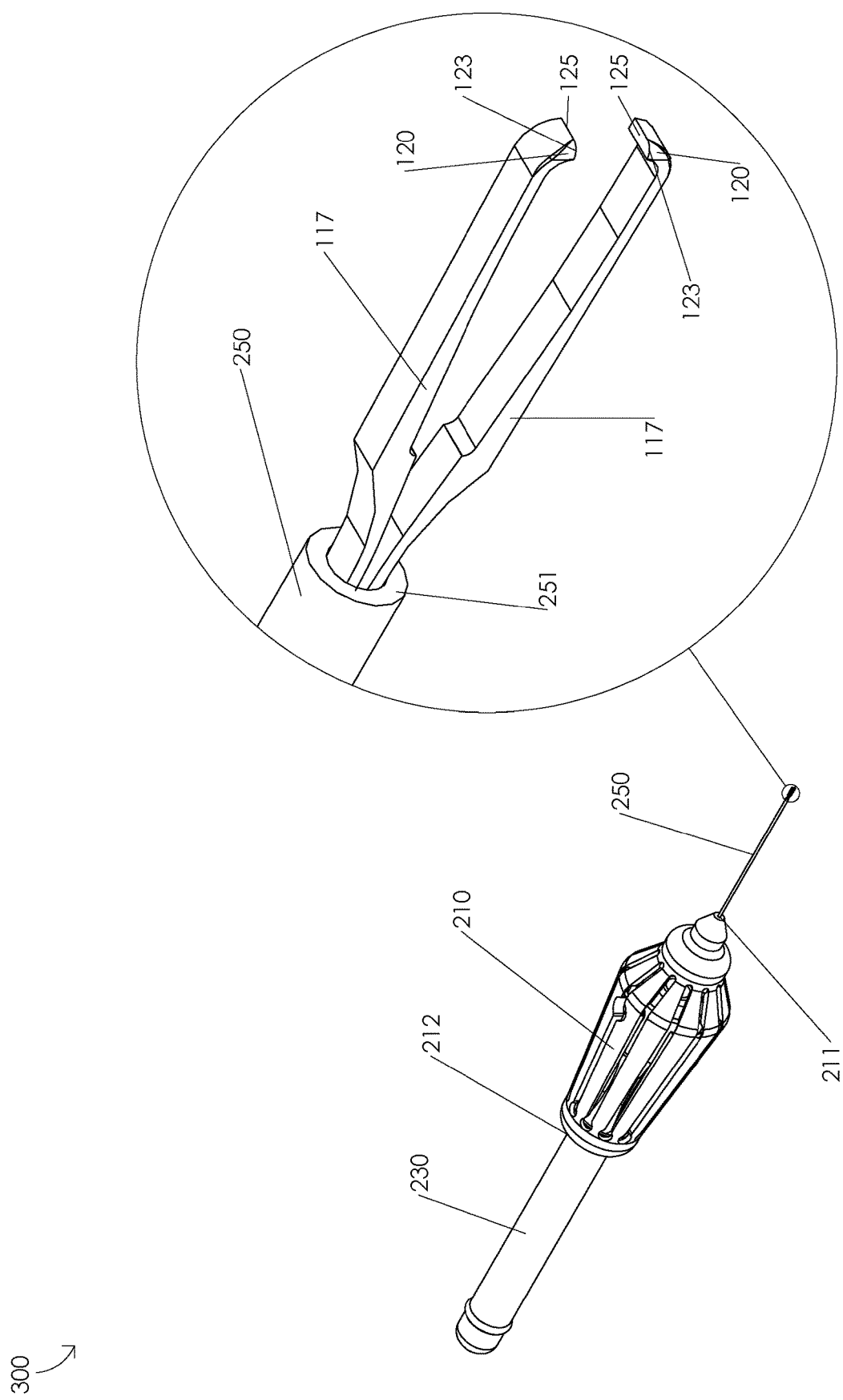
FIGS. 3A and 3B are schematic diagrams illustrating a closing of a membrane aggregating forceps tip.
Figure 3B:
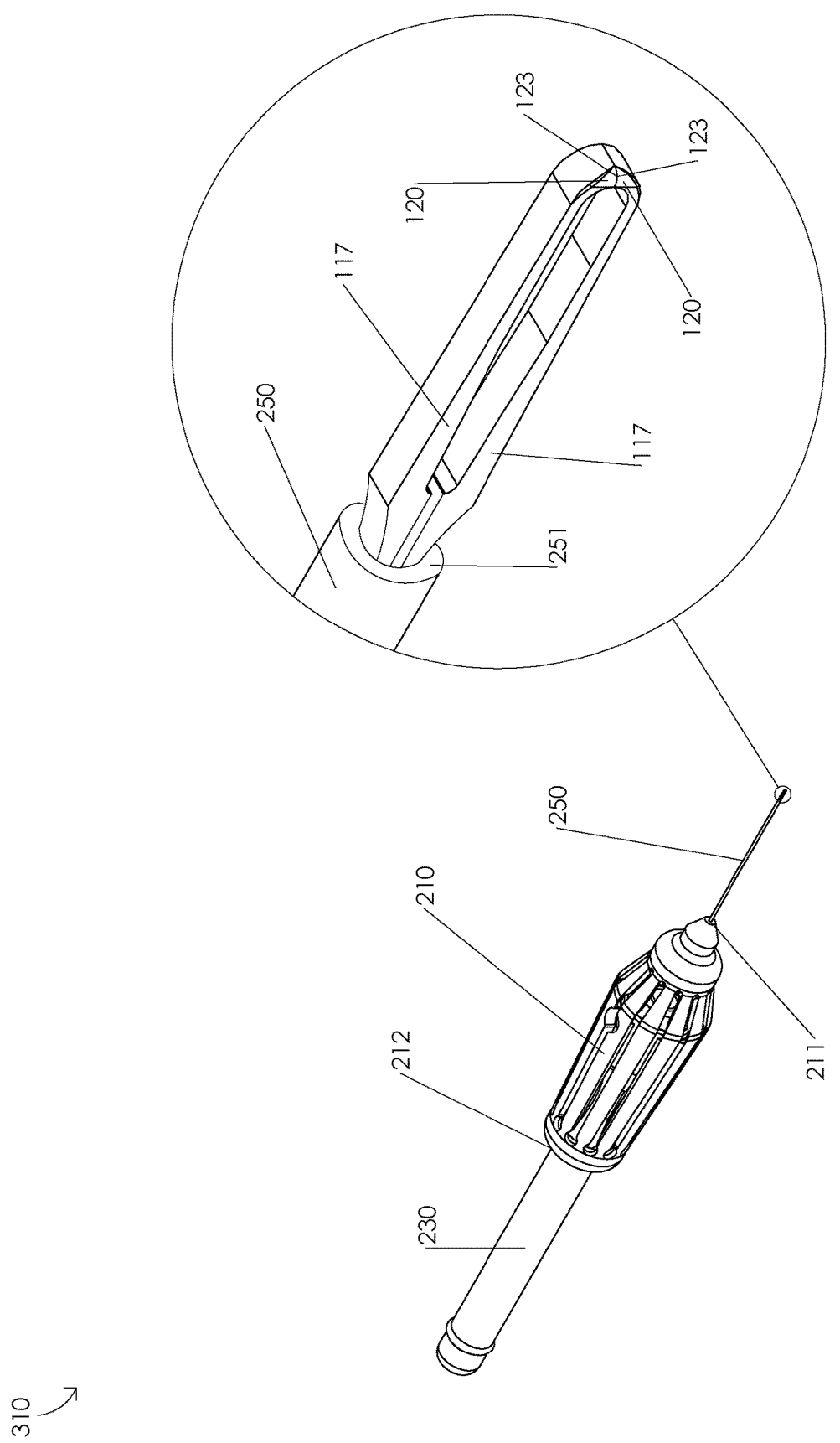

FIGS. 3A and 3B are schematic diagrams illustrating a closing of a membrane aggregating forceps tip 100. FIG. 3A illustrates an isometric view of an open membrane aggregating forceps 300. Illustratively, membrane aggregating forceps tip 100 may comprise an open membrane aggregating forceps 300 when actuation structure 210 is fully decompressed. In one or more embodiments, membrane aggregating forceps tip 100 may comprise an open membrane aggregating forceps 300 when first membrane aggregating forceps jaw 117 is fully separated from second membrane aggregating forceps jaw 117. Illustratively, membrane aggregating forceps tip 100 may comprise an open membrane aggregating forceps 300 when a portion of first membrane aggregating forceps jaw 117 is separated from a portion of second membrane aggregating forceps jaw 117 by a membrane aggregating forceps jaw maximum separation distance 129.

FIG. 3B illustrates an isometric view of a closed membrane aggregating forceps 310. In one or more embodiments, a compression of actuation structure 210 may be configured to extend hypodermic tube 250 relative to blank 110. Illustratively, a compression of actuation structure 210 may be configured to gradually close a membrane aggregating forceps tip 100 from an open membrane aggregating forceps 300 to a closed membrane aggregating forceps 310. In one or more embodiments, first medial jaw surface 125 may contact second medial jaw surface 125 when membrane aggregating forceps tip 100 comprises a closed membrane aggregating forceps 310. Illustratively, first membrane aggregating fillet 123 may contact second membrane aggregating fillet 123 when membrane aggregating forceps tip 100 comprises a closed membrane aggregating forceps 310. In one or more embodiments, membrane aggregating forceps tip 100 may comprise a closed membrane aggregating forceps 310 when actuation structure 210 is fully compressed.

Figure 4A:
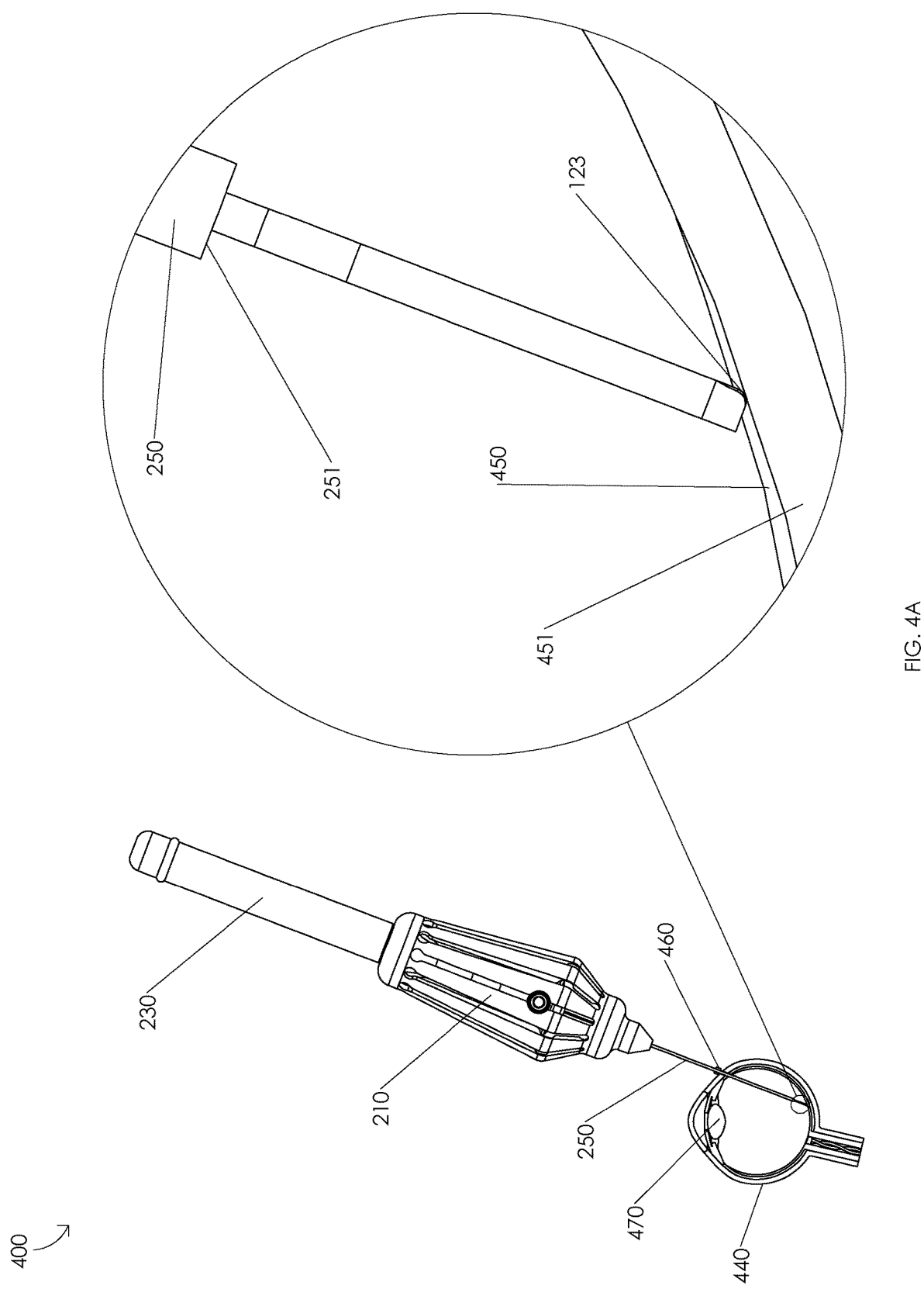
FIGS. 4A, 4B, 4C, and 4D are schematic diagrams illustrating a surgical procedure.

FIGS. 4A, 4B, 4C, and 4D are schematic diagrams illustrating a surgical procedure. FIG. 4A illustrates a posterior segment approach 400. Illustratively, a posterior segment approach 400 may be achieved through a cannula 460 disposed in an incision in a pars plana of an eye 440. In one or more embodiments, a surgeon may begin a posterior segment approach 400 by inserting membrane aggregating forceps tip 100, e.g., when membrane aggregating forceps tip 100 comprises a closed membrane aggregating forceps 310, and hypodermic tube 250 into cannula 460 and advancing membrane aggregating forceps tip 100 into an inner portion of eye 440 until curved medial projections 121 approach a retina 451. Illustratively, a surgeon may be required to perform a posterior segment approach 400 at an angle relative to a sagittal plane of eye 440 to avoid contacting lens capsule 470. In one or more embodiments, a surgeon may be required to perform a posterior segment approach 400 at an angle in a range of 19.0 to 23.0 degrees relative to a sagittal plane of eye 440 to avoid contacting lens capsule 470, e.g., a surgeon may be required to perform a posterior segment approach 400 at an angle of 21.0 degrees relative to a sagittal plane of eye 440 to avoid contacting lens capsule 470. Illustratively, a surgeon may be required to perform a posterior segment approach 400 at an angle of less than 19.0 degrees or greater than 23.0 degrees relative to a sagittal plane of eye 440 to avoid contacting lens capsule 470.

In one or more embodiments, membrane 450 may be disposed over a portion of retina 451. Illustratively, membrane 450 may comprise an internal limiting membrane. In one or more embodiments, membrane 450 may comprise an epiretinal membrane. Illustratively, a surgeon may be required to approach membrane 450 at an angle relative to a line normal to a surface of membrane 450 to avoid contacting lens capsule 470. In one or more embodiments, a surgeon may be required to approach membrane 450 at an angle in a range of 19.0 to 23.0 degrees relative to a line normal to a surface of membrane 450 to avoid contacting lens capsule 470, e.g., a surgeon may be required to approach membrane 450 at an angle of 21.0 degrees relative to a line normal to a surface of membrane 450 to avoid contacting lens capsule 470. Illustratively, a surgeon may be required to approach membrane 450 at an angle of less than 19.0 degrees or greater than 23.0 degrees relative to a line normal to a surface of membrane 450 to avoid contacting lens capsule 470.

Figure 4B:
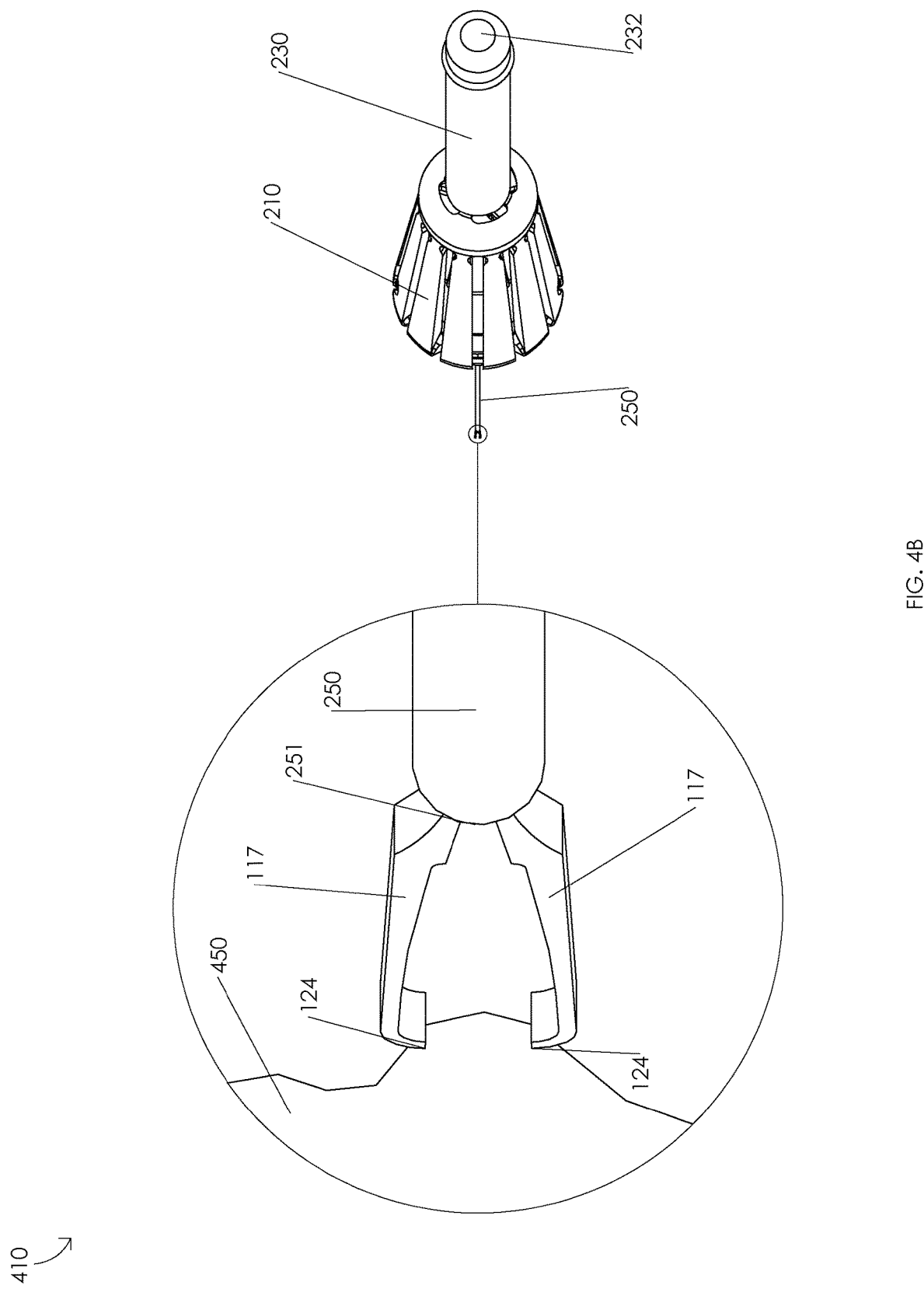

FIG. 4B illustrates a membrane approach 410. In one or more embodiments, a surgeon may perform a membrane approach 410 by orienting membrane aggregating forceps tip 100 wherein first distal jaw vertex 124 is superior to first membrane aggregating fillet 123, e.g., a surgeon may perform a membrane approach 410 by orienting membrane aggregating forceps tip 100 wherein second distal jaw vertex 124 is superior to second membrane aggregating fillet 123. Illustratively, a surgeon may perform a membrane approach 410 by orienting membrane aggregating forceps tip 100 wherein first membrane aggregating fillet 123 is inferior to first distal jaw vertex 124, e.g., a surgeon may perform a membrane approach 410 by orienting membrane aggregating forceps tip 100 wherein second membrane aggregating fillet 123 is inferior to second distal jaw vertex 124. In one or more embodiments, a surgeon may perform a membrane approach 410 by orienting membrane aggregating forceps tip 100 wherein first distal jaw vertex 124 is superior to first membrane socket 120, e.g., a surgeon may perform a membrane approach 410 by orienting membrane aggregating forceps tip 100 wherein second distal jaw vertex 124 is superior to second membrane socket 120. Illustratively, a surgeon may perform a membrane approach 410 by orienting membrane aggregating forceps tip 100 wherein first membrane socket 120 is inferior to first distal jaw vertex 124, e.g., a surgeon may perform a membrane approach 410 by orienting membrane aggregating forceps tip 100 wherein second membrane socket 120 is inferior to second distal jaw vertex 124. In one or more embodiments, a surgeon may perform a membrane approach 410 by approaching membrane 450 wherein a portion of first membrane aggregating forceps jaw 117 is separated from a portion of second membrane aggregating forceps jaw 117 by membrane aggregating forceps jaw maximum separation distance 129.

Figure 4C:
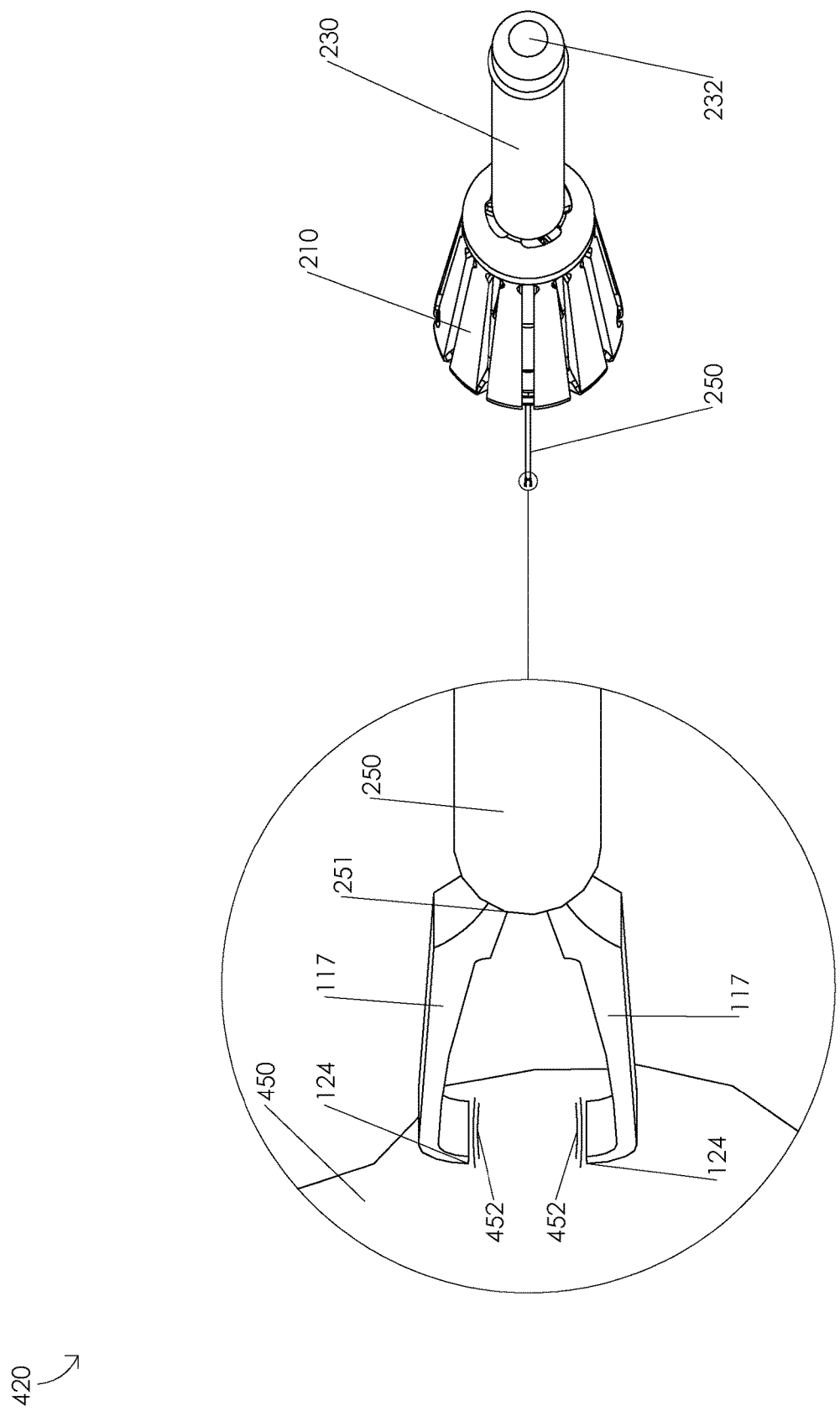

FIG. 4C illustrates a membrane aggregation 420. In one or more embodiments, a surgeon may perform a membrane aggregation 420 by disposing first membrane aggregating forceps jaw 117 and second membrane aggregating forceps jaw 117 over a portion of membrane 450 and compressing actuation structure 210. Illustratively, a surgeon may perform a membrane aggregation 420 by disposing first membrane aggregating fillet 123 and second membrane aggregating fillet 123 over a portion of membrane 450 and compressing actuation structure 210. In one or more embodiments, a surgeon may perform a membrane aggregation 420 by disposing first proximal membrane aggregating vertex 122 and second proximal membrane aggregating vertex 122 over a portion of membrane 450 and compressing actuation structure 210. Illustratively, a surgeon may perform a membrane aggregation 420 by disposing first distal membrane aggregating vertex 130 and second distal membrane aggregating vertex 130 over a portion of membrane 450 and compressing actuation structure 210. In one or more embodiments, a surgeon may perform a membrane aggregation 420 by disposing first membrane socket 120 and second membrane socket 120 over a portion of membrane 450 and compressing actuation structure 210. Illustratively, a surgeon may perform a membrane aggregation 420 by disposing first medial jaw surface 126 and second medial jaw surface 126 over a portion of membrane 450 and compressing actuation structure 210. In one or more embodiments, a surgeon may perform a membrane aggregation 420 by disposing first blunt edge 126 and second blunt edge 126 over a portion of membrane 450 and compressing actuation structure 210. Illustratively, a surgeon may perform a membrane aggregation 420 by disposing first curved medial projection 121 and second curved medial projection 121 over a portion of membrane 450 and compressing actuation structure 210. In one or more embodiments, a surgeon may perform a membrane aggregation 420 by disposing first distal jaw vertex 124 and second distal jaw vertex 124 over a portion of membrane 450 and compressing actuation structure 210. Illustratively, a surgeon may perform a membrane aggregation 420 by disposing first proximal jaw vertex 127 and second proximal jaw vertex 127 over a portion of membrane 450 and compressing actuation structure 210.

In one or more embodiments, disposing a portion of first membrane aggregating forceps jaw 117 and disposing a portion of second membrane aggregating forceps jaw 117 over a portion of membrane 450 and compressing actuation structure 210 may be configured to reduce a distance between first membrane aggregating forceps jaw 117 and second membrane aggregating forceps jaw 117. Illustratively, reducing a distance between first membrane aggregating forceps jaw 117 and second membrane aggregating forceps jaw 117 may be configured to aggregate membrane 450, e.g., reducing a distance between first membrane aggregating forceps jaw 117 and second membrane aggregating forceps jaw 117 may be configured to cause a membrane fold 452. In one or more embodiments, reducing a distance between first membrane aggregating forceps jaw 117 and second membrane aggregating forceps jaw 117 may be configured to cause a plurality of membrane folds 452. Illustratively, causing a membrane fold 452 may be configured to aggregate membrane 450 into an area between first membrane aggregating forceps jaw 117 and second membrane aggregating forceps jaw 117 wherein an amount of membrane 450 disposed between first membrane aggregating forceps jaw 117 and second membrane aggregating forceps jaw 117 may increase as a distance between first membrane aggregating forceps jaw 117 and second membrane aggregating forceps jaw 117 decreases.

In one or more embodiments, as a distance between first membrane aggregating forceps jaw 117 and second membrane aggregating forceps jaw 117 decreases, a portion of membrane 450 may be configured to ingress membrane socket 120, e.g., as a distance between first membrane aggregating forceps jaw 117 and second membrane aggregating forceps jaw 117 decreases, a first portion of membrane 450 may be configured to ingress a first membrane socket 120 and a second portion of membrane 450 may be configured to ingress a second membrane socket 120. Illustratively, as a distance between first membrane aggregating forceps jaw 117 and second membrane aggregating forceps jaw 117 decreases, a membrane fold 452 may be configured to ingress membrane socket 120, e.g., as a distance between first membrane aggregating forceps jaw 117 and second membrane aggregating forceps jaw 117 decreases, a first membrane fold 452 may be configured to ingress a first membrane socket 120 and a second membrane fold 452 may be configured to ingress a second membrane socket 120. In one or more embodiments, membrane aggregating fillet 123 may be configured to guide an ingress of a portion of membrane 450 into membrane socket 120, e.g., a first membrane aggregating fillet 123 may be configured to guide an ingress of a first portion of membrane 450 into a first membrane socket 120 and a second membrane aggregating fillet 123 may be configured to guide an ingress of a second portion of membrane 450 into a second membrane socket 120. Illustratively, membrane aggregating fillet 123 may be configured to guide an ingress of a membrane fold 452 into membrane socket 120, e.g., a first membrane aggregating fillet 123 may be configured to guide an ingress of a first membrane fold 452 into a first membrane socket 120 and a second membrane aggregating fillet 123 may be configured to guide an ingress of a second membrane fold 452 into a second membrane socket 120. In one or more embodiments, blunt edge 126 may be configured to guide an ingress of a portion of membrane 450 into membrane socket 120, e.g., a first blunt edge 126 may be configured to guide an ingress of a first portion of membrane 450 into a first membrane socket 120 and a second blunt edge 126 may be configured to guide an ingress of a second portion of membrane 450 into a second membrane socket 120. Illustratively, blunt edge 126 may be configured to guide an ingress of a membrane fold 452 into membrane socket 120, e.g., a first blunt edge 126 may be configured to guide an ingress of a first membrane fold 452 into a first membrane socket 120 and a second blunt edge 126 may be configured to guide an ingress of a second membrane fold 452 into a second membrane socket 120. In one or more embodiments, proximal membrane aggregating vertex 122 may be configured to guide an ingress of a portion of membrane 450 into membrane socket 120, e.g., a first proximal membrane aggregating vertex 122 may be configured to guide an ingress of a first portion of membrane 450 into a first membrane socket 120 and a second proximal membrane aggregating vertex 122 may be configured to guide an ingress of a second portion of membrane 450 into a second membrane socket 120. Illustratively, proximal membrane aggregating vertex 122 may be configured to guide an ingress of a membrane fold 452 into membrane socket 120, e.g., a first proximal membrane aggregating vertex 122 may be configured to guide an ingress of a first membrane fold 452 into a first membrane socket 120 and a second proximal membrane aggregating vertex 122 may be configured to guide an ingress of a second membrane fold 452 into a second membrane socket 120. In one or more embodiments, distal membrane aggregating vertex 130 may be configured to guide an ingress of a portion of membrane 450 into membrane socket 120, e.g., a first distal membrane aggregating vertex 130 may be configured to guide an ingress of a first portion of membrane 450 into a first membrane socket 120 and a second distal membrane aggregating vertex 130 may be configured to guide an ingress of a second portion of membrane 450 into a second membrane socket 120. Illustratively, distal membrane aggregating vertex 130 may be configure to guide an ingress of a membrane fold 452 into membrane socket 120, e.g., a first distal membrane aggregating vertex 130 may be configured to guide an ingress of a first membrane fold 452 into a first membrane socket 120 and a second distal membrane aggregating vertex 130 may be configured to guide an ingress of a second membrane fold 452 into a second membrane socket 120.

In one or more embodiments, a portion of membrane aggregating forceps tip 100 may be configured to prevent membrane 450 from shredding, tearing, fissuring, cleaving, splitting, ripping, or breaking during a surgical procedure, e.g., a portion of membrane aggregating forceps tip 100 may be configured to prevent membrane 450 from shredding, tearing, fissuring, cleaving, splitting, ripping, or breaking during a surgical procedure wherein membrane 450 is removed from retina 451. Illustratively, disposing a portion of first membrane aggregating forceps jaw 117 and a portion of second membrane aggregating forceps jaw 117 over membrane 450 and compressing actuation structure 210 may be configured to apply a force to a portion of membrane 450, e.g., disposing a portion of first membrane aggregating forceps jaw 117 and a portion of second membrane aggregating forceps jaw 117 over membrane 450 and compressing actuation structure 210 may be configured to apply a compressive force to a portion of membrane 450. In one or more embodiments, an application of a compressive force to a portion of membrane 450 may be configured to compress the portion of membrane 450, e.g., an application of a compressive force to a portion of membrane 450 may be configured to cause one or more membrane folds 452. Illustratively, disposing a portion of first membrane aggregating forceps jaw 117 and a portion of second membrane aggregating forceps jaw 117 over membrane 450 and compressing actuation structure 210 may be configured to apply a shear force to a portion of membrane 450. In one or more embodiments, an application of a shear force to a portion of membrane 450 may be configured to shear the portion of membrane 450, e.g., an application of a shear force to a portion of membrane 450 may be configured to cause one or more membrane folds 452. Illustratively, an application of a force to membrane 450 may be configured to cause membrane 450 to shred, tear, fissure, cleave, split, rip, or break, e.g., an application of a force to membrane 450 wherein a magnitude of the force exceeds a material strength of membrane 450 may be configured to cause membrane 450 to shred, tear, fissure, cleave, split, rip, or break, etc. In one or more embodiments, membrane socket 120 may be configured to prevent membrane 450 from shredding, tearing, fissuring, cleaving, splitting, ripping, or breaking during a surgical procedure, e.g., membrane socket 120 may be configured to facilitate an expansion of membrane 450. Illustratively, membrane socket 120 may be configured to facilitate an expansion of a portion of membrane 450 into membrane socket 120 wherein the expansion of the portion of membrane 450 into membrane socket 120 prevents a magnitude of a force applied to membrane 450 from exceeding a material strength of membrane 450. In one or more embodiments, membrane aggregating fillet 123 may be configured to prevent membrane 450 from shredding, tearing, fissuring, cleaving, splitting, ripping, or breaking during a surgical procedure, e.g., membrane aggregating fillet 123 may be configured to distribute a force applied to membrane. Illustratively, membrane aggregating fillet 123 may be configured to distribute a force applied to membrane 450 wherein the distribution of the force applied to membrane 450 prevents a magnitude of the force applied to membrane 450 from exceeding a material strength of membrane 450. In one or more embodiments, blunt edge 126 may be configured to prevent membrane 450 from shredding, tearing, fissuring, cleaving, splitting, ripping, or breaking during a surgical procedure, e.g., blunt edge 126 may be configured to distribute a force applied to membrane. Illustratively, blunt edge 126 may be configured to distribute a force applied to membrane 450 wherein the distribution of the force applied to membrane 450 prevents a magnitude of the force applied to membrane 450 from exceeding a material strength of membrane 450.

Figure 4D:
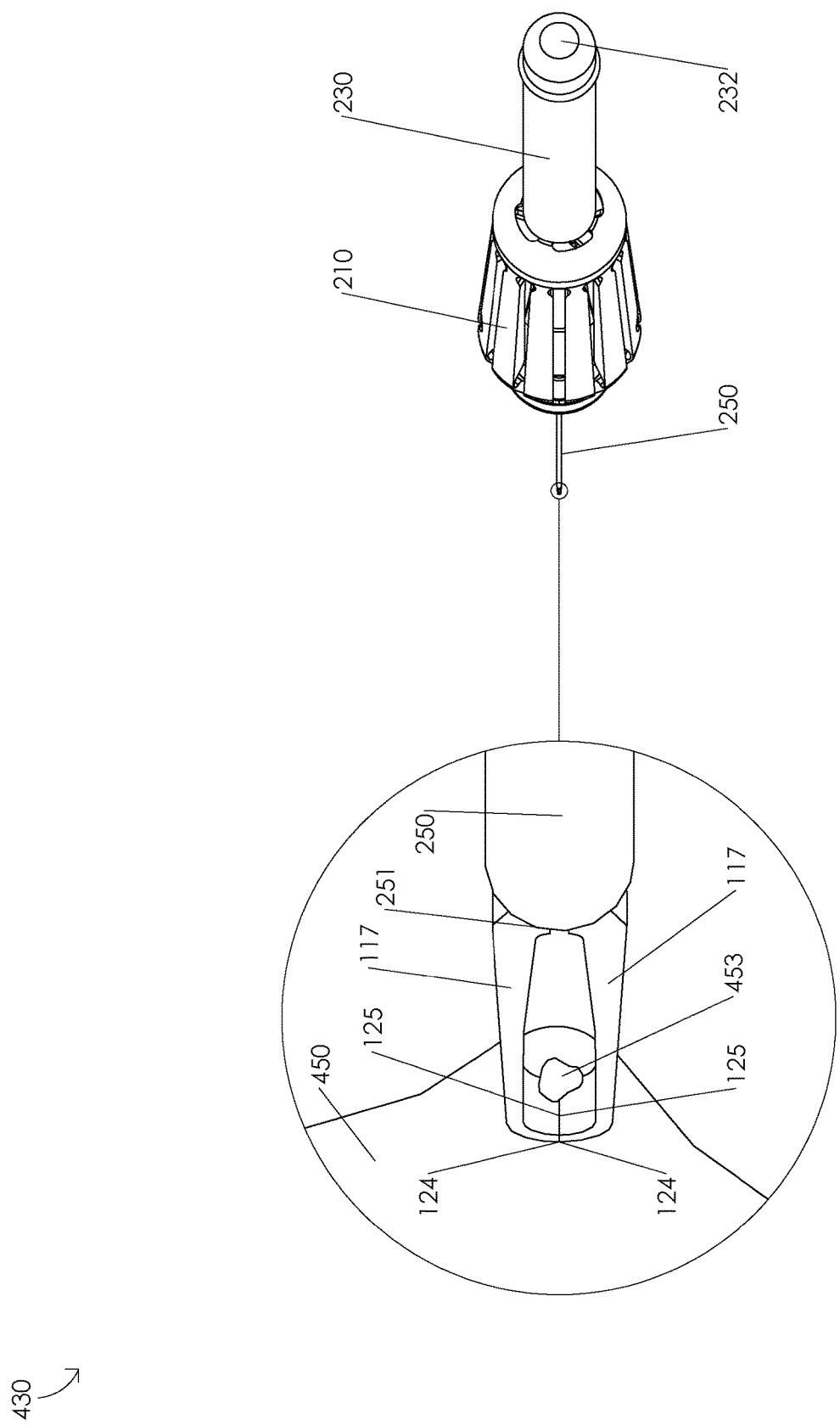

FIG. 4D illustrates a membrane grab 430. In one or more embodiments, a surgeon may perform a membrane grab 430 by disposing first membrane aggregating forceps jaw 117 and second membrane aggregating forceps jaw 117 over a portion of membrane 450 and compressing actuation structure 210. Illustratively, a surgeon may perform a membrane grab 430 by disposing first membrane aggregating fillet 123 and second membrane aggregating fillet 123 over a portion of membrane 450 and compressing actuation structure 210. In one or more embodiments, a surgeon may perform a membrane grab 430 by disposing first proximal membrane aggregating vertex 122 and second proximal membrane aggregating vertex 122 over a portion of membrane 450 and compressing actuation structure 210. Illustratively, a surgeon may perform a membrane grab 430 by disposing first distal membrane aggregating vertex 130 and second distal membrane aggregating vertex 130 over a portion of membrane 450 and compressing actuation structure 210. In one or more embodiments, a surgeon may perform a membrane grab 430 by disposing first membrane socket 120 and second membrane socket 120 over a portion of membrane 450 and compressing actuation structure 210. Illustratively, a surgeon may perform a membrane grab 430 by disposing first medial jaw surface 126 and second medial jaw surface 126 over a portion of membrane 450 and compressing actuation structure 210. In one or more embodiments, a surgeon may perform a membrane grab 430 by disposing first blunt edge 126 and second blunt edge 126 over a portion of membrane 450 and compressing actuation structure 210. Illustratively, a surgeon may perform a membrane grab 430 by disposing first curved medial projection 121 and second curved medial projection 121 over a portion of membrane 450 and compressing actuation structure 210. In one or more embodiments, a surgeon may perform a membrane grab 430 by disposing first distal jaw vertex 124 and second distal jaw vertex 124 over a portion of membrane 450 and compressing actuation structure 210. Illustratively, a surgeon may perform a membrane grab 430 by disposing first proximal jaw vertex 127 and second proximal jaw vertex 127 over a portion of membrane 450 and compressing actuation structure 210.

In one or more embodiments, a surgeon may perform a membrane grab 430 by performing a membrane aggregation 420 and compressing actuation structure 210. Illustratively, as a distance between first membrane aggregating forceps jaw 117 and second membrane aggregating forceps jaw 117 decreases, a portion of membrane 450 may be configured to ingress membrane socket 120, e.g., as a distance between first membrane aggregating forceps jaw 117 and second membrane aggregating forceps jaw 117 decreases, a first portion of membrane 450 may be configured to ingress a first membrane socket 120 and a second portion of membrane 450 may be configured to ingress a second membrane socket 120. In one or more embodiments, as a distance between first membrane aggregating forceps jaw 117 and second membrane aggregating forceps jaw 117 decreases, a first portion of membrane 450 may be configured to ingress membrane socket 120 and the first portion of membrane 450 may be configured to egress membrane socket 120, e.g., a first portion of membrane 450 may be configured to ingress membrane socket 120 and the first portion of membrane 450 may be configured to egress membrane socket 120 wherein the first portion of membrane 450 comprises a grasped portion 453. Illustratively, as a portion of membrane 450 ingresses membrane socket 120 and then egresses membrane socket 120 the portion of membrane 450 comprises a grasped portion 453.

For example, a portion of membrane 450 may be configured to ingress membrane socket 120 from a distal side of curved medial projection 121 and the portion of membrane 450 may be configured to egress membrane socket 450 on a proximal side of curved medial projection 121. In one or more embodiments, as a distance between first membrane aggregating forceps jaw 117 and second membrane aggregating forceps jaw 117 decreases, a first portion of membrane 450 may be configured to ingress membrane socket 120 and the first portion of membrane 450 may be configured to egress membrane socket 120 and a second portion of membrane 450 may be configured to ingress membrane socket 120, e.g., a first portion of membrane 450 may be configured to ingress membrane socket 120 and the first portion of membrane 450 may be configured to egress membrane socket 120 and a second portion of membrane 450 may be configured to ingress membrane socket 120 wherein the first portion of membrane 450 comprises a grasped portion 453. Illustratively, as a first portion of membrane 450 ingresses membrane socket 120 and a second portion of membrane 450 egresses membrane socket 120 the second portion of membrane 450 comprises a grasped portion 453, e.g., the first portion of membrane 450 may displace the second portion of membrane 450 in membrane socket 120. For example, a first portion of membrane 450 may be configured to ingress membrane socket 120 from a distal side of curved medial projection 121 and a second portion of membrane 450 may be configured to egress membrane socket 450 on a proximal side of curved medial projection 121. In one or more embodiments, as a distance between first membrane aggregating forceps jaw 117 and second membrane aggregating forceps jaw 117 decreases, a first portion of membrane 450 may be configured to ingress membrane socket 120 and the first portion of membrane 450 may be configured to egress membrane socket 120 and a second portion of membrane 450 may be configured to ingress membrane socket 120 and the second portion of membrane 450 may be configured to egress membrane socket 120 and a third portion of membrane 450 may be configured to ingress membrane socket 120, e.g., a first portion of membrane 450 may be configured to ingress membrane socket 120 and the first portion of membrane 450 may be configured to egress membrane socket 120 and a second portion of membrane 450 may be configured to ingress membrane socket 120 and the second portion of membrane 450 may be configured to egress membrane socket 120 and a third portion of membrane 450 may be configured to ingress membrane socket 120 wherein the first portion of membrane 450 and the second portion of membrane 450 comprise a grasped portion 453. Illustratively, as a first portion of membrane 450 ingresses membrane socket 120 and a second portion of membrane 450 egresses membrane socket 120 and as a third portion of membrane 450 ingresses membrane socket and the first portion of membrane 450 egresses membrane socket 120 the second portion of membrane 450 and the first portion of membrane comprise a grasped portion 453. In one or more embodiments, membrane aggregating fillet 123 may be configured to guide an egress of membrane 450 out of membrane socket 120, e.g., membrane aggregating fillet 123 may be configured to guide a portion of membrane 450 into a grasped portion 453. Illustratively, blunt edge 126 may be configured to guide an egress of membrane 450 out of membrane socket 120, e.g., blunt edge 126 may be configured to guide a portion of membrane 450 into a grasped portion 453. In one or more embodiments, blunt edge 126 may be configured to guide an ingress of a first portion of membrane 450 into membrane socket 120 and membrane aggregating fillet 123 may be configured to guide an egress of the first portion of membrane 450 out from membrane socket 120, e.g., blunt edge 126 may be configured to guide an ingress of a first portion of membrane 450 into membrane socket 120 and membrane aggregating fillet 123 may be configured to guide an egress of the first portion of membrane 450 out from membrane socket 120 wherein the first portion of membrane 450 comprises a grasped portion 453. Illustratively, blunt edge 126 may be configured to guide an ingress of a first portion of membrane 450 into membrane socket 120 and membrane aggregating fillet 123 may be configured to guide an egress of a second portion of membrane 450 out from membrane socket 120, e.g., blunt edge 126 may be configured to guide an ingress of a first portion of membrane 450 into membrane socket 120 and membrane aggregating fillet 123 may be configured to guide an egress of a second portion of membrane 450 out from membrane socket 120 wherein the second portion of membrane 450 comprises a grasped portion 453. In one or more embodiments, blunt edge 126 may be configured to guide an ingress of a first portion of membrane 450 into membrane socket 120 and membrane aggregating fillet 123 may be configured to guide an egress of a second portion of membrane 450 out from membrane socket 120 and blunt edge 126 may be configured to guide an ingress of a third portion of membrane 450 into membrane socket 120 and membrane aggregating fillet 123 may be configured to guide an egress of the first portion of membrane 450 out from membrane socket 120, e.g., blunt edge 126 may be configured to guide an ingress of a first portion of membrane 450 into membrane socket 120 and membrane aggregating fillet 123 may be configured to guide an egress of a second portion of membrane 450 out from membrane socket 120 and blunt edge 126 may be configured to guide an ingress of a third portion of membrane 450 into membrane socket 120 and membrane aggregating fillet 123 may be configured to guide an egress of the first portion of membrane 450 out from membrane socket 120 wherein the first portion of membrane 450 and the second portion of membrane 450 comprise a grasped portion 453.

In one or more embodiments, a surgeon may remove membrane 450 from retina 451 by applying a force to grasped portion 453, e.g., a surgeon may remove membrane 450 from retina 451 by applying a tensile force to grasped portion 453. Illustratively, a surgeon may remove membrane 450 from retina 451 by applying a force to grasped portion 453 when a size of grasped portion 453 exceeds a size of membrane socket 120, e.g., a surgeon may remove membrane 450 from retina 451 by applying a force to grasped portion 453 when a size of grasped portion 453 exceeds a combined size of first membrane socket 120 and second membrane socket 120. In one or more embodiments, a surgeon may remove membrane 450 from retina 451 without causing substantial trauma to retina 451. Illustratively, a size of grasped portion 453 may be configured for use in full-thickness macular hole surgery, e.g., a size of grasped portion 453 may be configured for use in full-thickness macular hole surgery with an inverted internal limiting membrane flap. In one or more embodiments, a size of grasped portion 453 may be configured for use in large full-thickness macular hole surgery. Illustratively, a size of grasped portion may be configured for use in myopic macular hole surgery.

The foregoing description has been directed to particular embodiments of this invention. It will be apparent; however, that other variations and modifications may be made to the described embodiments, with the attainment of some or all of their advantages. Specifically, it should be noted that the principles of the present invention may be implemented in any system. Furthermore, while this description has been written in terms of a surgical instrument, the teachings of the present invention are equally suitable to any systems where the functionality may be employed. Therefore, it is the object of the appended claims to cover all such variations and modifications as come within the true spirit and scope of the invention.

What is claimed is:

1. An instrument comprising:
   an actuation structure having an actuation structure distal end and an actuation structure proximal end;
   a hypodermic tube having a hypodermic tube distal end and a hypodermic tube proximal end;
   a blank wherein the blank is disposed in the hypodermic tube and the actuation structure;
   a first membrane aggregating forceps jaw of the blank;
   a first curved medial projection of the first membrane aggregating forceps jaw;
   a first proximal membrane aggregating vertex of the first curved medial projection;
   a first medial jaw surface of the first curved medial projection;
   a first blunt edge of the first curved medial projection;
   a first membrane socket of the first curved medial projection;
   a first membrane aggregating fillet of the first curved medial projection wherein the first membrane aggregating fillet is disposed between the first membrane socket and the first medial jaw surface;
   a second membrane aggregating forceps jaw of the blank;
   a second curved medial projection of the second membrane aggregating forceps jaw;
   a second medial jaw surface of the second curved medial projection;
   a second blunt edge of the second curved medial projection;
   a second membrane socket of the second curved medial projection; and
   a second membrane aggregating fillet of the second curved medial projection wherein the second membrane aggregating fillet is disposed between the second membrane socket and the second medial jaw surface.

2. The instrument of claim 1 further comprising:
   a distal membrane aggregating vertex of the first curved medial projection.

3. The instrument of claim 1 further comprising:
   a proximal jaw vertex of the first curved medial projection.

4. The instrument of claim 1 further comprising:
   a distal jaw vertex of the first curved medial projection.

5. The instrument of claim 1 wherein a compression of the actuation structure is configured to decrease a distance between the first membrane aggregating forceps jaw and the second membrane aggregating forceps jaw.

6. The instrument of claim 1 wherein a decompression of the actuation structure is configured to increase a distance between the first membrane aggregating forceps jaw and the second membrane aggregating forceps jaw.

7. The instrument of claim 1 wherein a compression of the actuation structure is configured to extend the hypodermic tube relative to the blank.

8. The instrument of claim 1 wherein a decompression of the actuation structure is configured to retract the hypodermic tube relative to the blank.

9. The instrument of claim 1 further comprising:
   a removable handle having a removable handle distal end and a removable handle proximal end wherein a portion of the removable handle is disposed in an inner chamber proximal taper of the actuation structure.

10. The instrument of claim 9 further comprising:
    a plurality of fingers of the actuation structure, the plurality of fingers disposed in the inner chamber proximal taper of the actuation structure.

11. The instrument of claim 10 further comprising:
    a barb head of the removable handle.

12. The instrument of claim 10 further comprising:
    a barb base of the removable handle.

13. The instrument of claim 10 further comprising:
    a barb channel of the removable handle.

14. An instrument comprising:
    an actuation structure having an actuation structure distal end and an actuation structure proximal end;
    a hypodermic tube having a hypodermic tube distal end and a hypodermic tube proximal end;
    a blank wherein the blank is disposed in the hypodermic tube and the actuation structure;
    a first membrane aggregating forceps jaw of the blank;
    a first curved medial projection of the first membrane aggregating forceps jaw;
    a first medial jaw surface of the first curved medial projection;
    a first blunt edge of the first curved medial projection;
    a first membrane socket of the first curved medial projection;
    a first proximal membrane aggregating vertex of the first curved medial projection;
    a first membrane aggregating fillet of the first curved medial projection wherein the first membrane aggregating fillet is disposed between the first membrane socket and the first medial jaw surface;
    a second membrane aggregating forceps jaw of the blank;
    a second curved medial projection of the second membrane aggregating forceps jaw;
    a second medial jaw surface of the second curved medial projection;
    a second blunt edge of the second curved medial projection;
    a second membrane socket of the second curved medial projection;
    a second proximal membrane aggregating vertex of the second curved medial projection; and
    a second membrane aggregating fillet of the second curved medial projection wherein the second membrane aggregating fillet is disposed between the second membrane socket and the second medial jaw surface.

15. The instrument of claim 14 further comprising:
a distal membrane aggregating vertex of the first curved medial projection.

16. The instrument of claim 14 further comprising:
a proximal jaw vertex of the first curved medial projection.

17. The instrument of claim 14 further comprising:
a distal jaw vertex of the first curved medial projection.

18. An instrument comprising:
an actuation structure having an actuation structure distal end and an actuation structure proximal end;
a hypodermic tube having a hypodermic tube distal end and a hypodermic tube proximal end;
a blank wherein the blank is disposed in the hypodermic tube and the actuation structure;
a first membrane aggregating forceps jaw of the blank;
a first curved medial projection of the first membrane aggregating forceps jaw;
a first medial jaw surface of the first curved medial projection;
a first blunt edge of the first curved medial projection;
a first membrane socket of the first curved medial projection;
a first distal membrane aggregating vertex of the first curved medial projection;
a first proximal membrane aggregating vertex of the first curved medial projection;
a first membrane aggregating fillet of the first curved medial projection wherein the first membrane aggregating fillet is disposed between the first membrane socket and the first medial jaw surface;
a second membrane aggregating forceps jaw of the blank;
a second curved medial projection of the second membrane aggregating forceps jaw;
a second medial jaw surface of the second curved medial projection;
a second blunt edge of the second curved medial projection;
a second membrane socket of the second curved medial projection;
a second distal membrane aggregating vertex of the second curved medial projection;
a second proximal membrane aggregating vertex of the second curved medial projection; and
a second membrane aggregating fillet of the second curved medial projection wherein the second membrane aggregating fillet is disposed between the second membrane socket and the second medial jaw surface.

19. The instrument of claim 18 further comprising:
a proximal jaw vertex of the first curved medial projection.

* * * * *